United States Patent
Tanigawa

Patent Number: 6,083,369
Date of Patent: Jul. 4, 2000

[54] HEATER CONTROL SYSTEM FOR AN AIR-FUEL RATIO SENSOR IN AN INTERNAL COMBUSTION ENGINE

[75] Inventor: Hiroshi Tanigawa, Mishima, Japan

[73] Assignee: Toyota Jidosha Kabushiki Kaisha, Toyota, Japan

[21] Appl. No.: 09/021,843

[22] Filed: Feb. 11, 1998

[30] Foreign Application Priority Data

Feb. 21, 1997 [JP] Japan .................................. 9-037943

[51] Int. Cl.[7] .................................................. G01N 27/26
[52] U.S. Cl. ...................... 204/424; 219/202; 219/490; 219/497
[58] Field of Search .................................. 204/406, 424, 204/425, 421, 426, 427, 428, 408; 73/23.32; 123/697; 219/202, 209, 490, 497

[56] References Cited

U.S. PATENT DOCUMENTS

| | | | |
|---|---|---|---|
| 4,365,604 | 12/1982 | Sone .................................... | 204/424 |
| 4,504,732 | 3/1985 | Bube et al. ........................... | 219/202 |
| 4,938,196 | 7/1990 | Hoshi et al. .......................... | 123/489 |
| 4,947,819 | 8/1990 | Takahashi et al. .................... | 204/406 |
| 5,011,590 | 4/1991 | Nakajima et al. .................... | 204/408 |
| 5,037,761 | 8/1991 | Barnett et al. ....................... | 204/425 |
| 5,330,719 | 7/1994 | Barnett et al. ....................... | 204/408 |
| 5,580,477 | 12/1996 | Oota et al. ........................... | 219/202 |

FOREIGN PATENT DOCUMENTS

| | | |
|---|---|---|
| 533037 A1 | 3/1993 | European Pat. Off. . |
| 58-82149 | 5/1983 | Japan . |
| 3-246461 | 11/1991 | Japan . |
| 4-276111 | 2/1993 | Japan . |

*Primary Examiner*—Robert J. Warden, Sr.
*Assistant Examiner*—Kaj K. Olsen
*Attorney, Agent, or Firm*—Oliff & Berridge PLC

[57] ABSTRACT

A heater control system for an air-fuel ratio sensor for an internal combustion engine is provided to supply power to a heater in order to activate the air-fuel ratio sensor quickly at the time of starting the engine. The system comprises an air-fuel ratio sensor arranged in the engine exhaust system for detecting the air-fuel ratio, a heater for heating the air-fuel ratio sensor, a power supply including a battery and an alternator for supplying power to the heater, a power switch for operating a power line for transmitting power from the power supply, a capacitor circuit charged by the power supply and adapted to discharge through the heater the electricity stored therein by the charging, a first switch connected in series with the heater for supplying or cutting off the current flowing to the heater, and a control unit for controlling the first switch to close after the power switch is closed. The system further comprises another capacitor circuit adapted to be connected in parallel to the power supply at the time of charging and to be connected in series with the power supply at the time of discharging to thereby apply to the heater a high voltage obtained by superimposing the charge voltage of the capacitor circuit on the source voltage. At and subsequent to the time of starting the engine, the power supplied to the heater is controlled in such a manner as to maintain the air-fuel ratio sensor in an active state.

42 Claims, 16 Drawing Sheets

| RELAY $R_3$ | RELAY $R_4$ | MODE |
|---|---|---|
| OFF | OFF | MODE 1 |
| OFF | ON | MODE 2 |
| ON | OFF | MODE 3 |
| ON | ON | MODE 4 |

HEATER CONTROL SYSTEM FOR AN AIR-FUEL RATIO SENSOR IN AN INTERNAL COMBUSTION ENGINE

BACKGROUND OF THE INVENTION

1. Field of the Invention

The present invention relates to a heater control system for an air-fuel ratio sensor of an internal combustion engine or, in particular, to a heater control system for an air-fuel ratio sensor of an internal combustion engine for supplying power to a heater in such a manner as to activate the air-fuel ratio sensor quickly when the engine starts.

2. Description of the Related Art

A heater control system for an air-fuel ratio sensor arranged in the exhaust system of an internal combustion engine has been proposed (in JPP No. 3-246461), in which, in order to activate the air-fuel ratio sensor quickly when the engine starts, a high voltage is applied to a heater for heating the air-fuel ratio sensor immediately after starting the engine, in which the time when the air-fuel ratio sensor is activated is detected by the fact that the voltage between two porous electrodes of an electrochemical sensor cell has dropped below a predetermined value, and in which the voltage applied to the heater is subsequently reduced to a low voltage. In a generally-used conventional heater control operation for the air-fuel ratio sensor, a battery voltage is applied to the heater at a predetermined duty cycle, and this duty factor is set to, say, 100% until the air-fuel ratio sensor is activated and subsequently to, say, 50%. This heater control operation will be explained below.

FIG. 17 is a diagram schematically showing a configuration of a heater control system for an air-fuel ratio sensor of an internal combustion engine according to the prior art. FIG. 18 is a time chart of the voltage applied to the heater, the heater temperature and the sensor element temperature of the heater control system shown in FIG. 17. As shown in FIG. 17, a heater 1 is heated by being supplied with power from a power supply including a battery 2 and an alternator 20, and thereby activates the air-fuel ratio sensor (not shown). The current is supplied or cut off to the heater 1 by closing and opening a first switch SW1. SW1 is composed of a FET, for example, and is arranged in a control means 5 for controlling the power supplied to the heater 1. An external terminal T1 of the control means 5 is connected to the battery 2 through an ignition switch IGSW and a fuse F2, an external terminal T2 is grounded, and an external terminal T3 is connected to an end of the heater 1. Terminals BA, ON and ST of the ignition switch IGSW are connected to the positive electrode of the battery 2, the fuse F2 for the external load and the fuse F1 for the heater 1, respectively.

When the ignition switch IGSW is turned on from off state, the voltage across the battery 2 is applied to the heater 1 through the fuse F1. When the control means 5 turns-on the switch SW1 subsequently, a current flows in the heater 1. The current flowing in the heater 1 is detected by a current detection circuit 11 based on the voltage across a current detection resistor $r_{11}$ arranged in the control means 5. The voltage applied to the heater 1, on the other hand, is detected by detecting the voltages at the external terminals T1 and T3 and determined from the difference therebetween. The voltage at the external terminal T1, i.e., the voltage across the battery 2 is detected by an electronic control unit (ECU) not shown, while the voltage at the external terminal T3 is detected-by a voltage detection circuit 12. The ECU is composed of a digital computer and includes a ROM (read-only memory), a RAM (random access memory), a backup RAM, a CPU (microprocessor), and input and output ports connected to each other by a bidirectional bus. The FET used as the switch SW1 is turned on and off by a current control circuit 13 connected to the output port of the ECU. Now, the control operation of the current control circuit 13 will be explained.

In FIG. 18, the abscissa represents the time, and the ordinate represents the voltage applied to the heater for a curve $V_a$, the heater temperature for a curve $T_a$, and the sensor element temperature for a curve $T_b$. At time point $t_0$ when the ignition switch IGSW is turned on, the voltage $V_B$ across the battery 2 is directly applied to the heater 1. At this time, the voltage $V_{HT}$ applied to the heater 1 is equal to $V_B$. At time $t_1$ when the engine is started, i.e., when the ignition switch IGSW is turned to position ST, the ECU starts to drive a starter motor not shown. Thus the voltage $V_B$ across the battery 2 (indicated by the curve $V_a$) drops sharply. With the rotation of the starter motor, the alternator 20 generates power and begins to charge the battery 2. Consequently, $V_B$ begins to rise gradually, and after passing a predetermined voltage $V_{TH}$ at time point $t_2$, reaches the maximum output voltage $V_{ALT}$ of the alternator 20. In order for the voltage drop across the battery 2 not to adversely affect the startability of the engine, the current begins to be supplied to the heater at time point $t_2$.

With the rise in the temperature of the heater 1, the sensor element is heated. The heater temperature (indicated by curve $T_a$) and the sensor element temperature (indicated by curve $T_b$) rise until time point $t_3$ when the alternator 20 produces a maximum output voltage. After that, at time point $t_4$, the sensor element reaches an activation temperature $T_{th}$ of, say, 650° C., indicating an active state, thus making it possible to measure the air-fuel ratio (A/F). At and after time point $t_4$, the temperature of the heater 1 is controlled in such a manner as to maintain the active state of the sensor element. The temperature of the heater can be controlled by various methods. They include a method in which the resistance value of the heater is measured and controlled at a constant value, a method in which the power supplied to the heater is controlled based on a power map prepared in accordance with the operating conditions of the engine, and a method in which the resistance value of the sensor element is measured and controlled at a constant value.

A method of controlling the power supplied to the heater will be briefly described below. The sensor element, which is arranged in the exhaust pipe, receives the heat from the exhaust gas as well as from the heater arranged in the exhaust pipe, and further receives the radiation heat from the exhaust pipe and the engine body. As a result, the temperature of the sensor element is affected not only by the temperature of the heater but also by the temperature of the exhaust gas and the temperature of the engine body. In view of this, power is supplied to the heater based on the basic electric energy determined in accordance with the operating conditions of the engine. Specifically, the lower the load under which the engine running, i.e. the lower the exhaust gas temperature, the higher the level to which the basic electric energy of the heater is set. The higher the load under which the engine is running, i.e., the higher the exhaust gas temperature, on the other hand, the lower the level at which the basic electric energy of the heater is set. Also, this basic electric energy is determined experimentally in such a manner as to maintain the temperature of the sensor element in the range of 650° C. to 750° C. in order to maintain the sensor element in active state.

The above-mentioned control method will be specifically explained. The resistance value of the heater 1 is calculated from the current flowing in the heater 1 detected by the current detection circuit 11 and the voltage applied to the heater 1 detected by the voltage detection circuit 12. From the resistance value of the heater 1, the temperature of the heater 1 proportional to the particular resistance value is calculated. Power is then supplied to the heater 1 in such a manner that the temperature of the heater 1 may be maintained at a sufficient level to hold the air-fuel ratio sensor in an active state. Also, the power supplied to the heater 1 is controlled by turning on and off the switch SW1 in a predetermined duty cycle in accordance with the duty factor calculated based on the basic electric energy corresponding to the operating conditions of the engine.

By the way, in the system proposed in JPP No. 3-246461 described above and in a generally-used conventional heater control system for an air-fuel ratio sensor, the voltage applied to the air-fuel ratio sensor has an upper limit thereof determined by the performance of the battery and the alternator mounted on the vehicle carrying the engine. In rapidly heating the air-fuel ratio sensor, the restriction imposed by the particular upper limit poses the problem that the air-fuel ratio sensor cannot be activated at a sufficiently early time.

Another possible method for rapidly heating the air-fuel ratio sensor is increasing the current by reducing the resistance value of the heater while maintaining constant the voltage supplied to the heater. The problem hampering the realization of this method is the fact that the increase in heater size and the improvement in the material have their own limits and lead to a high cost.

Also, in these conventional systems, the supply of current to the heater is inhibited during the cranking of the engine in order to secure the starter performance, i.e., the startability of the engine. This gives rise to the problem that the activation of the air-fuel sensor is further delayed.

SUMMARY OF THE INVENTION

The object of the present invention is to solve the above-mentioned problems and to provide a heater control system for an air-fuel ratio sensor of an internal combustion engine in which power is supplied to the heater in such a manner as to activate the air-fuel ratio sensor at an early time when starting the engine.

A heater control system for an air-fuel ratio sensor of an internal combustion engine according to the present invention intended to solve the above-mentioned problems comprises an air-fuel ratio sensor arranged in the exhaust system of an internal combustion engine for detecting the air-fuel ratio of the engine, a heater for heating the air-fuel ratio sensor, a power supply including a battery and an alternator for supplying power to the heater, and a power switch for opening or closing a power line for transmitting power to a load including the heater from the power supply, and controls the power supplied to the heater in such a manner as to maintain the active state of the air-fuel ratio sensor. The system is characterized in that it comprises a capacitor circuit adapted to be charged by the power supply and to discharge, through the heater, the electricity stored by the charging.

FIG. 1 is a diagram showing a basic configuration of a heater control system for an air-fuel ratio sensor of an internal combustion engine according to a first aspect of the invention. A heater control system for an air-fuel ratio sensor of an internal combustion engine according to the first aspect for solving the above-mentioned problems comprises an air-fuel ratio sensor arranged in the exhaust system of the internal combustion engine for detecting the air-fuel ratio of the engine, a heater 1 for heating the air-fuel ratio sensor, a power supply including a battery 2 and an alternator 20 for supplying power to the heater 1, a power switch 10 adapted to open and close a power line for transmitting power to a load including the heater 1 from the power supply, a means for controlling the power supplied to the heater 1 in such a manner as to maintain the active state of the air-fuel ratio sensor, a capacitor circuit 3 adapted to be charged by the power supply and to discharge through the heater 1 the electricity stored by the charging, a first switch 4 connected in series to the heater 1 for supplying or cutting off the current flowing to the heater 1, and a control means 5 for controlling the first switch 4 to close after the power switch 10 is closed.

In the above-mentioned configuration, when the power switch 10 is closed and the capacitor circuit 3 is charged, the control means 5 closes the first switch 4, so that power is supplied from the power supply to the heater 1, while at the same time discharging through the heater 1 the electricity stored in the capacitor circuit 3, thus activating the heater 1 quickly.

The heater control system for an air-fuel ratio sensor of an internal combustion engine according to the first aspect of the invention further comprises a second switch 6 interposed between the power supply and the capacitor circuit for supplying or cutting off the charge current to the capacitor circuit 3 from the power supply.

By opening this second switch 6 during the cranking of the engine, power ceases to be supplied to the heater 1 from the power supply including the battery 2 and the alternator 20 during the cranking. The voltage drop across the battery 2 constituting the power supply which otherwise might be caused by the power consumption by the heater 1 thus is eliminated, and the startability of the engine is secured. In the process, power is supplied from the capacitor circuit 3 to the heater 1.

In the heater control system for an air-fuel ratio sensor of an internal combustion engine according to the first aspect of the invention, the control means 5 controls the first switch 4 to close from the beginning of the cranking of the engine.

In this control operation, the first switch 4 is closed after the power switch 10 is closed and after the engine cranking begins. Therefore, wasteful power consumption is avoided which might be caused in the case where the first switch 4 is closed immediately after the power switch 10 is closed to supply power to the heater 1 and where the engine fails to start for a long time or completely.

In the heater control system for an air-fuel ratio sensor of an internal combustion engine according to the first aspect of the invention, the control means 5 controls the first switch 4 to open or close in accordance with the engine cranking condition after the power switch 10 is closed.

This control operation is performed in such a manner that the first switch 4 is closed only when the cranking condition is stable, and therefore the startability of the engine is prevented from being deteriorated. The stability of the engine cranking condition is judged by detecting the engine speed, the change in engine speed, the voltage drop across the battery, the engine water temperature, etc. and by checking whether these factors meet reference values.

The heater control system for an air-fuel ratio sensor of an internal combustion engine according to the first aspect of the invention comprises a heater temperature detection means for detecting the temperature of the heater 1. The control means 5 controls the first switch 4 to open when the temperature of the heater 1 detected by the heater temperature detection means exceeds a predetermined level and to close when such a temperature is not higher than the predetermined level while the engine is cranking after the closing of the first switch 4.

The battery, if degenerated, cannot be sufficiently charged by the alternator and fails to contribute to supplying power to the heater. In view of this, the above-mentioned control operation is performed in such a way as to open the first switch 4 when the heater temperature exceeds a predetermined level sufficient to maintain the air-fuel ratio sensor in active state and to close the first switch 4 when the heater temperature is not higher than the predetermined level, thereby preventing wasteful power consumption of the heater. Since the resistance value of the heater is proportional to the heater temperature, the heater temperature detection means measures the voltage applied to the heater and the current flowing therein, for example, calculates the resistance value of the heater, and thus determines the heater temperature by conversion from the resistance value of the heater.

The heater control system for an air-fuel ratio sensor of an internal combustion engine according to the first aspect of the invention further comprises a fault judging means for detecting the voltage applied to the heater 1 when the second switch 6 is open and judging a fault of the capacitor circuit 3 on the basis of the detected voltage.

When a fault is judged, the operator can be informed of a malfunction of the system. Also, the second switch 6 can prevent discharge of the capacitor circuit 3 after the engine stops.

The heater control system for an air-fuel ratio sensor of an internal combustion engine according to the first aspect of the invention further comprises a third switch 7 connected the capacitor circuit 3 for supplying or cutting off the charge current or discharge current for the capacitor circuit 3. In the case where a fault is judged by the fault judging means, the control means 5 controls the first switch 4 to close after the end of engine cranking, while at the same time setting the third switch 7 to the normally open state.

During the time period after a fault judgement to the repair or replacement of the system, the system can thus be safely used. Also, the second switch 7 prevents the capacitor circuit 3 from being discharged after the engine stops.

FIG. 2A is a diagram showing a basic configuration of the heater control system for an air-fuel ratio sensor of an internal combustion engine according to the second aspect of the invention when it is in charged state, and FIG. 2B is a similar diagram showing the same heater control system in discharged state. The heater control system for an air-fuel ratio sensor of an internal combustion engine according to the second aspect of the invention that solves the above-mentioned problems comprises an air-fuel ratio sensor arranged in the exhaust system of the internal combustion engine for detecting the air-fuel ratio of the engine, a heater 1 for heating the air-fuel ratio sensor, a power supply including a battery 2 and an alternator 20 for supplying power to the heater 1, a power switch 10 for opening or closing a power line for transmitting power to a load including the heater 1 from the power supply, a means for controlling the power supplied to the heater 1 in such a way as to keep the air-fuel ratio sensor in active state, a capacitor circuit 8 charged by the power supply and adapted to discharge, through the heater 1, the electricity stored therein by the charging, a charge-discharge switching circuit 9 for connecting the power supply and the capacitor circuit 8 in parallel to each other and connecting the heater 1 in series to the parallel circuit including the power supply and the capacitor circuit 8 to form a charge circuit at the time of charging the capacitor circuit 8 while connecting the power supply, the capacitor circuit 8 and the heater 1 in series to each other to form a discharge circuit at the time of discharging the capacitor circuit 8, a first switch 4 connected in series to the heater 1 for supplying or cutting off the current flowing to the heater 1, and a control means 5 for controlling the first switch 4 to close from the time when the engine cranking starts after the power switch is closed and controlling the charge-discharge switching circuit 9 in such a manner as to form the above-mentioned charge circuit when the air-fuel ratio sensor is in active state and to form the above-mentioned discharge circuit when the air-fuel ratio sensor is inactive.

With the above-mentioned configuration, after the power switch 10 is closed, the control means 5 switches the charge-discharge switching circuit 9 to form a charging circuit for the capacitor circuit 8, and from the time when the engine crank starts, closes the first switch 4 while at the same time controlling the charge-discharge switching circuit 9 in such a way as to form a charge circuit when the air-fuel ratio sensor is active and to form a discharge circuit when the air-fuel ratio sensor is inactive. At the time of forming a discharging circuit, power is supplied from the power supply to the heater 1, and the electricity stored in the capacitor circuit 8 is discharged through the heater 1, thus activating the heater 1 quickly.

In the heater control system for an air-fuel ratio sensor of an internal combustion engine according to the second aspect of the invention, the control means 5 controls the first switch 4 to close and controls the charge-discharge switching circuit 9 to switch from the charge circuit to the discharge circuit at the end of the engine cranking.

This control operation closes the first switch 4 and switches the charge-discharge switching circuit 9 from the charge circuit to the discharge circuit at the end of engine cranking. Therefore, power is not supplied from the power supply to the heater 1 during the cranking, and the voltage drop across the battery 2, making up the power supply, due to the power consumption by the heater 1 is eliminated, thus securing the startability of the engine.

The heater control system for an air-fuel ratio sensor of an internal combustion engine according to the second aspect of the invention further comprises a fault judging means for detecting the voltage applied to the heater at the time of charging and discharging the capacitor circuit 8 and judging a fault of the capacitor circuit 8 from the voltage difference detected.

A fault judgement can inform the operator of a malfunction of the system.

In the heater control system for an air-fuel ratio sensor of an internal combustion engine according to the second aspect of the invention, the control means 5 controls the first switch 4 to close at the end of engine cranking and switches at least one of the terminals of the capacitor circuit 8 connected to the charge-discharge switching circuit 9 to the normally-open state upon judgement of a fault by the fault judging means.

A fault judgement permits the system to be used safely, subsequently, until the system is repaired or replaced.

In the heater control system for an air-fuel ratio sensor of an internal combustion engine according to the second aspect of the invention, the capacitor circuit 8 includes a plurality of capacitors connected in parallel to each other.

The above-mentioned configuration can reduce the number of capacitors used.

In the heater control system for an air-fuel ratio sensor of an internal combustion engine according to the second aspect of the invention, the capacitor 8 includes a plurality of capacitors connected in series with each other.

This configuration eliminates the need of setting a charge voltage by a voltage-dividing resistor.

The heater control system for an air-fuel ratio sensor of an internal combustion engine according to the second aspect of the invention further comprises a diode D adapted to be connected to the power line in parallel to the capacitor circuit 8 at the time of discharge of the capacitor circuit 8.

This configuration suppresses the drop of the voltage applied to the heater at the time of discharge.

The heater control system for an air-fuel ratio sensor of an internal combustion engine according to the second aspect of the invention further comprises a resistor r adapted to be interposed between the negative electrode of the capacitor circuit 8 and the ground at the time of charging the capacitor circuit 8.

This configuration can suppress the source voltage variations, if any, at the time of charging or discharging the capacitor.

In the heater control system for an air-fuel ratio sensor of an internal combustion engine according to the second aspect of the invention, the capacitor circuit 8 includes a plurality of capacitors, the system further comprising a switching means for switching the discharge voltage pattern of the capacitor circuit 8.

The above-mentioned configuration can optimize the source voltage derived from the battery and the alternator, the charge voltage of the capacitors, and the voltage applied to the heater in accordance with the heater temperature.

In the heater control system for an air-fuel ratio sensor of an internal combustion engine according to the second aspect of the invention, the switching circuit includes at least a switch operated to switch the capacitor 8 between a series connection and a parallel connection.

This configuration can optimize the source voltage derived from the battery and the alternator, the charge voltage of the capacitors, and the voltage applied to the heater in accordance with the heater temperature.

In the heater control system for an air-fuel ratio sensor of an internal combustion engine according to the second aspect of the invention, the switching means includes a switch operated to inhibit the discharge of a part of the capacitors.

This configuration can optimize the source voltage derived from the battery and the alternator, the charge voltage of the capacitors, and the voltage applied to the heater in accordance with the heater temperature.

In the heater control system for an air-fuel ratio sensor of an internal combustion engine according to the second aspect of the invention, all the capacitors of the capacitor circuit 8 are connected in series with each other at the time of charging, the system further comprising a resistor $r_0$ inserted between the negative electrode of the capacitor circuit 8 and the ground.

This configuration can suppress the source voltage variations, if any, at the time of charging or discharging the capacitors.

FIG. 3A is a diagram showing a basic configuration of the heater control system for an air-fuel ratio sensor of an internal combustion engine in charged state, and FIG. 3B a similar diagram showing the same system in discharged state. The heater control system for an air-fuel ratio sensor of an internal combustion engine according to a third aspect of the invention for solving the above-mentioned problems comprises an air-fuel ratio sensor arranged in the exhaust system of the internal combustion engine for detecting the air-fuel ratio of the engine, a heater 1 for heating the air-fuel ratio sensor, a power supply including a battery 2 and an alternator 20 for supplying power to the heater 1, and a power switch for opening or closing a power line for transmitting power to a load including the heater 1 from the power supply, a means for controlling the power supplied to the heater 1 in such a way as to maintain the air-fuel ratio sensor in active state, a first capacitor circuit 3 and a second capacitor circuit 8 charged by the power supply and adapted to discharge through the heater 1 the electricity stored by charging, a charge-discharge switching circuit 9 for connecting the second capacitor circuit 8 in parallel to the first capacitor connected in parallel to the power supply while at the same time connecting the second capacitor circuit 8 and the heater 1 in series to the parallel circuit including the power supply and the first capacitor circuit 3 thereby to form a charge circuit at the time of charging the second capacitor circuit 8 on the one hand, and for connecting the second capacitor circuit 8 and the heater 1 in series to the first capacitor circuit 3 connected in parallel to the power supply thereby to form a discharge circuit at the time of discharging the second capacitor circuit 8 on the other hand, a first switch 4 connected in series to the heater 1 for supplying or cutting off the current flowing to the heater 1, and a control means 5 for controlling the first switch 4 to close after the power switch 10 is closed and for controlling the charge-discharge switching circuit 9 from the start of engine cranking in such a manner as to form a charge circuit when the air-fuel ratio sensor is active and to form a discharge circuit when the air-fuel ratio sensor is inactive.

With the above-mentioned configuration, after the power switch 10 is closed, the control means 5 closes the first switch 4 while at the same time switching the charge-discharge switching circuit 9 to form a charge circuit for the second capacitor circuit 8, thus charging the first capacitor circuit 3 and the second capacitor circuit 8. After the cranking begins, on the other hand, the first switch 4 is closed and the charge-discharge switching circuit 9 is controlled to form a charge circuit when the air-fuel ratio sensor is active and to form a discharge circuit when the air-fuel ratio sensor is inactive. As a result, at the time of forming a discharge circuit, power is supplied from the power supply and the first capacitor circuit 3 to the heater 1 and the electricity stored in the second capacitor circuit 8 is discharged through the heater 1, thus activating the heater 1 quickly.

The heater control system for an air-fuel ratio sensor of an internal combustion engine according to the third aspect of the invention further comprises a second switch 6 arranged between the power supply on the one hand and the first capacitor circuit 3 and the second capacitor circuit 8 on the other for supplying or cutting off the charging current from the power supply to the first capacitor circuit 3 and the second capacitor circuit 8.

In the case where the second switch 6 is opened during the engine cranking, power ceases to be supplied to the heater 1 from the power supply. Thus the voltage drop across the battery 2 constituting the power supply which otherwise might be caused by the power consumption by the heater 1 is eliminated thereby to secure the startability of the engine.

In the meantime, power is supplied to the heater 1 from the first capacitor circuit 3 and the second capacitor circuit 8.

In the heater control system for an air-fuel ratio sensor of an internal combustion engine according to a third aspect of the invention, the control means 5 controls the first switch 4 to close from the time when the engine starts cranking.

As a result of this control operation, the first switch 4 is closed from the time when the engine begins cranking after the power switch 10 is closed. It is therefore possible to save the wasteful power consumption which might be caused in the case where the first switch 4 is closed immediately after the power switch 10 is closed to supply power to the heater 1 and where the engine fails to start for a long time or completely.

In the heater control system for an air-fuel ratio sensor of an internal combustion engine according to the third aspect of the invention, the control means 5 controls the first switch 4 to open or close in accordance with the engine cranking condition after the power switch 10 is closed.

This control operation closes the first switch 4 only when the engine cranking is stable, and can thereby prevent the deterioration of the engine startability. The stability of the engine cranking condition is judged by detecting the engine speed, the change in engine speed, the voltage drop across the battery, the engine water temperature, etc. and by checking whether these factors meet reference values.

The heater control system for an air-fuel ratio sensor of an internal combustion engine according to the third aspect of the invention further comprises a heater temperature detection means for detecting the temperature of the heater 1, wherein the control means 5 controls the first switch 4 to open when the temperature of the heater 1 detected by the heater temperature detection means exceeds a predetermined level and to close when the temperature of the heater 1 is not higher than the predetermined level during the cranking after the engine starts cranking and the first switch 4 is closed subsequently.

In the case where the battery is degenerated, the battery cannot be sufficiently charged by the alternator and cannot contribute to supplying power to the heater. In such a case, the above-mentioned control operation is performed to open the first switch 4 when the heater temperature exceeds a predetermined level sufficiently high to maintain the air-fuel ratio sensor in active state and to close the first switch 4 when the heater temperature is not higher than the predetermined level, thus preventing wasteful power consumption by the heater. The heater temperature detection means, taking advantage of the fact that the resistance value of the heater is proportional to the heater temperature, calculates the resistance value of the heater by measuring the voltage applied to the heater and the current flowing therein thereby and determines the heater temperature by conversion from the resistance value of the heater.

The heater control system for an air-fuel ratio sensor of an internal combustion engine according to the third aspect of the invention further comprises a first fault judging means for detecting the voltage applied to the heater 1 when the second switch 6 is open and judging a fault of the first capacitor circuit 3 from the voltage thus detected.

A fault judgement can inform the operator of a malfunction of the system. Also, a second switch 6 can prevent the capacitor circuit 3 from being discharged after the engine stops.

The heater control system for an air-fuel ratio sensor of an internal combustion engine according to the third aspect of the invention further comprises a third switch 7 connected in series with the first capacitor circuit 3 for supplying or cutting off the charge current and the discharge current for the first capacitor circuit 3, wherein, upon a fault judgement by the first fault judging means, the control means 5 controls the first switch 4 to be closed and controls the third switch 7 to be normally open from the time when the engine stops cranking.

In this way, until the system is repaired or replaced after the fault judgement, the system can be used safely. Also, the third switch 7 prevents the discharge from the capacitor circuit 3 after the engine stops.

The heater control system for an air-fuel ratio sensor of an internal combustion engine according to the third aspect of the invention further comprises a second fault judging means for detecting the voltage applied to the heater 1 at the time of charging and discharging the first capacitor circuit 3 and the second capacitor circuit 8, respectively, and judging a fault of the second capacitor 8 from the difference between the two voltages thus detected.

This fault judgement can inform the operator of a malfunction of the system.

In the heater control system for an air-fuel ratio sensor of an internal combustion engine according to the third aspect of the invention, the control means 5, upon a fault judgement by the second fault judging means, controls the first switch 4 to close at the end of engine cranking and to switch at least one of the terminals of the second capacitor circuit 8 connected to the charge-discharge switching circuit 9 to a normally open state.

Until the system is repaired or replaced after this fault judgement, therefore, the system-can be used safely.

In the heater control system for an air-fuel ratio sensor of an internal combustion engine according to the third aspect of the invention, the second capacitor circuit 8 includes a plurality of capacitors connected in parallel with each other.

This configuration can reduce the number of capacitors used.

In the heater control system for an air-fuel ratio sensor of an internal combustion engine according to the third aspect of the invention, the second capacitor circuit 8 includes a plurality of capacitors connected in series with each other.

This configuration eliminates the need of setting a charge voltage by a voltage-dividing resistor.

The heater control system for an air-fuel ratio sensor of an internal combustion engine according to the third aspect of the invention further comprises a diode D connected to a power line in parallel to the second capacitor circuit 8 at the time of discharging the second capacitor circuit 8.

This configuration suppresses the drop of the voltage applied to the heater at the time of discharge.

The heater control system for an air-fuel ratio sensor of an internal combustion engine according to the third aspect of the invention further comprises a resistor $r_0$ inserted between the negative electrode of the second capacitor circuit 8 and the ground at the time of charging the second capacitor circuit 8.

This configuration can suppress the source voltage variations, if any, at the time of charging or discharging the capacitors.

In the heater control system for an air-fuel ratio sensor of an internal combustion engine according to the third aspect of the invention, the second capacitor circuit 8 includes a plurality of capacitors and the system further comprises a switching means for switching the discharge voltage pattern for the second capacitor circuit 8.

This configuration can optimize the source voltage derived from the battery and the alternator, the charge voltage for the capacitors and the voltage applied to the heater in accordance with the heater temperature.

In the heater control system for an air-fuel ratio sensor of an internal combustion engine according to the third aspect of the invention, the switching means includes at least a switch operated to switch the second capacitor circuit 8 between series and parallel connections.

This configuration can optimize the source voltage generated by the battery and the alternator, the charge voltage for the capacitors and the voltage applied to the heater in accordance with the heater temperature.

In the heater control system for an air-fuel ratio sensor of an internal combustion engine according to the third aspect of the invention, the switching means includes a switch operated to inhibit the discharging of a part of the capacitors.

This configuration can optimize the source voltage generated by the battery and the alternator, the charge voltage for the capacitors and the voltage applied to the heater in accordance with the heater temperature.

In the heater control system for an air-fuel ratio sensor of an internal combustion engine according to the third aspect of the invention, all the capacitors of the second capacitor circuit 8 are connected in series to each other and a resistor is inserted between the negative electrode of the second capacitor circuit 8 and the ground at the time of charging.

This configuration can suppress the source voltage variations, if any, at the time of charging or discharging the capacitors.

BRIEF DESCRIPTION OF THE DRAWINGS

The present invention will be more clearly understood from the description as set forth below with reference to the accompanying drawings, wherein.

DESCRIPTION OF THE PREFERRED EMBODIMENTS

The preferred embodiments of the present invention will be described below with reference to the accompanying drawings.

Figure 1:
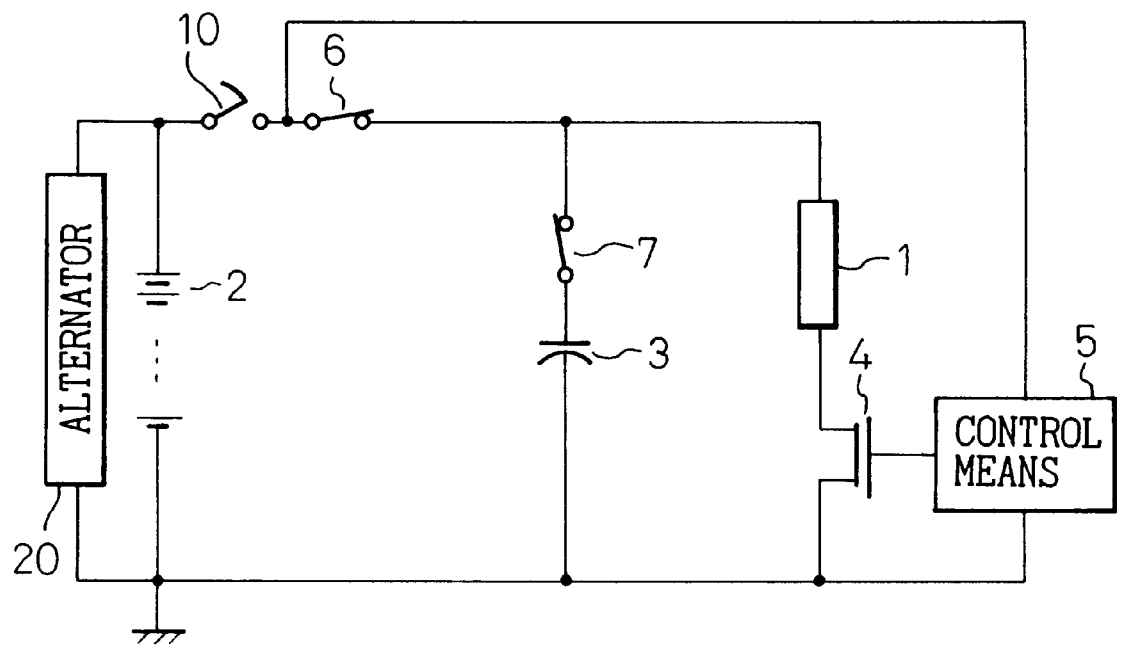
FIG. 1 is a diagram showing a basic configuration of a heater control system for an air-fuel ratio sensor of an internal combustion engine according to a first aspect of the present invention.
Figure 2A:
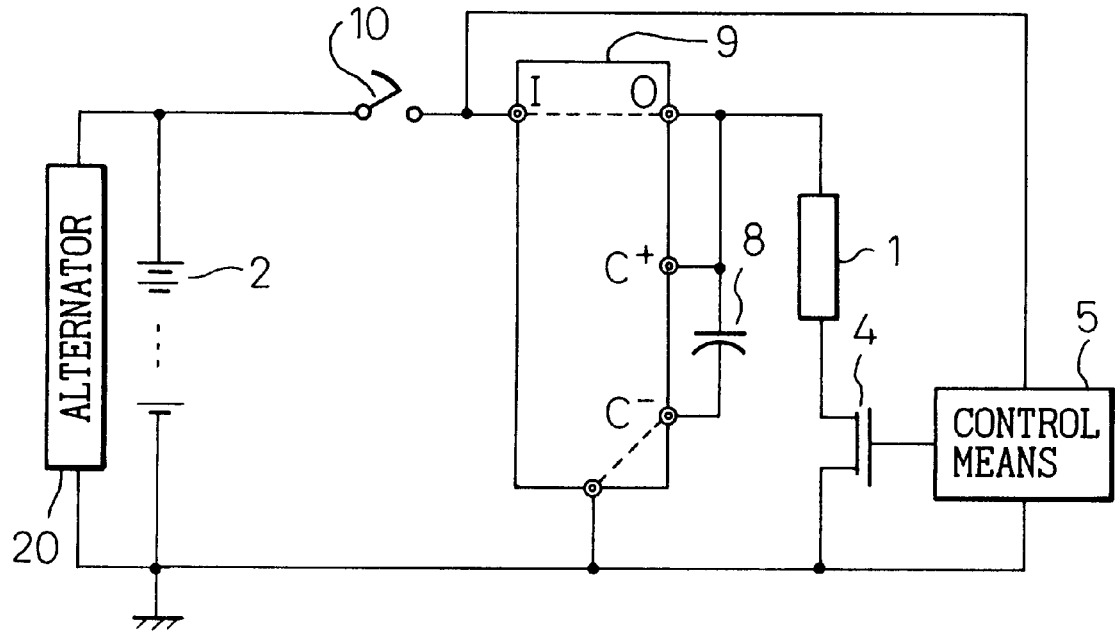
FIG. 2A is a diagram showing a basic configuration of a heater control system in charged state for an air-fuel ratio sensor of an internal combustion engine according to a second aspect of the present invention.
Figure 2B:
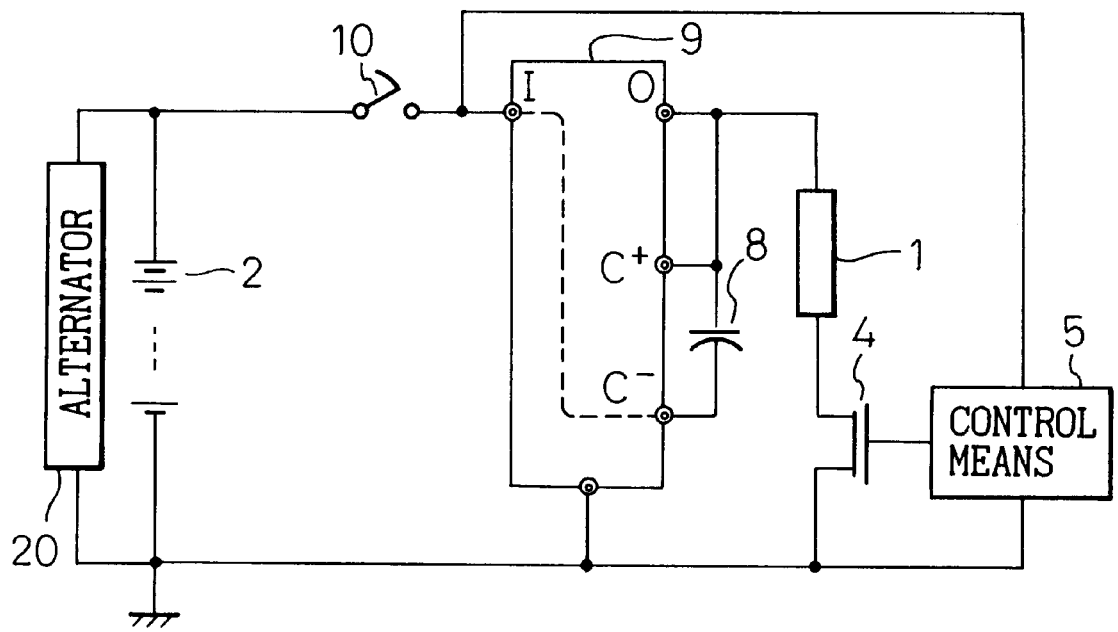
FIG. 2B is a diagram showing a basic configuration of the heater control system of FIG. 2A in discharged state.
Figure 3A:
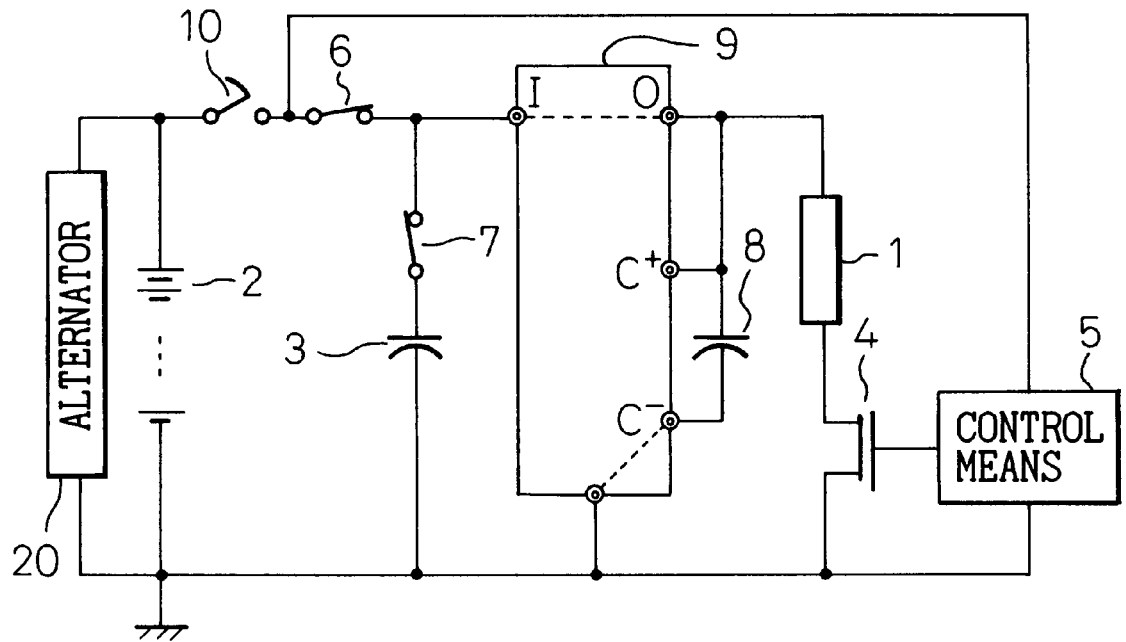
FIG. 3A is a diagram showing a basic configuration of a heater control system in charged state for an air-fuel ratio sensor of an internal combustion engine according to a third aspect of the present invention.
Figure 3B:
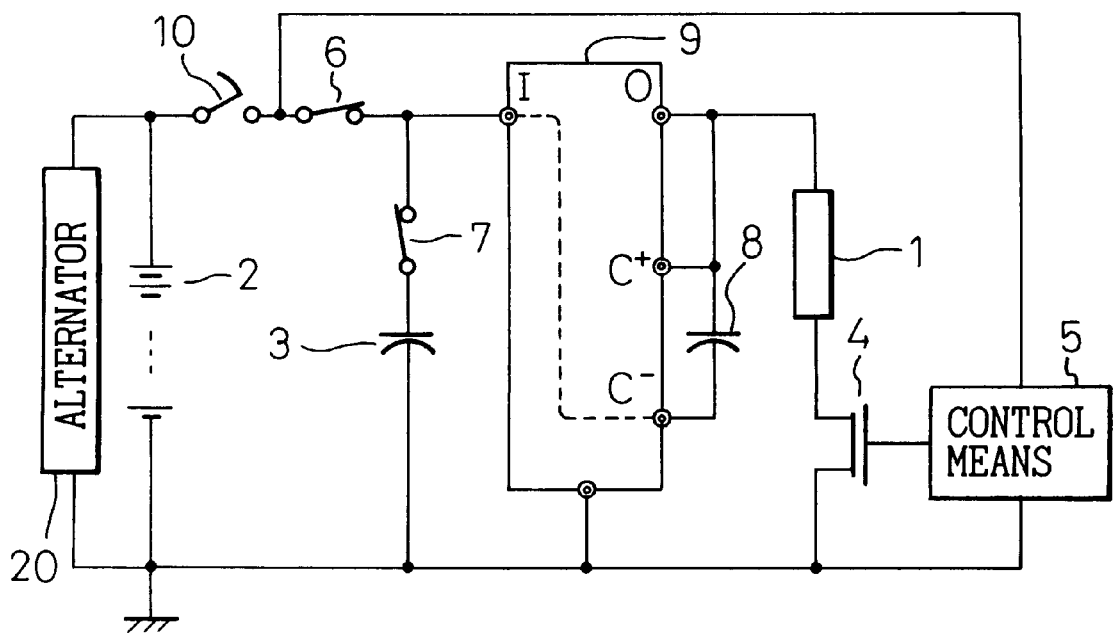
FIG. 3B is a diagram showing a basic configuration of the heater control system of FIG. 3A in discharged state.
Figure 4:
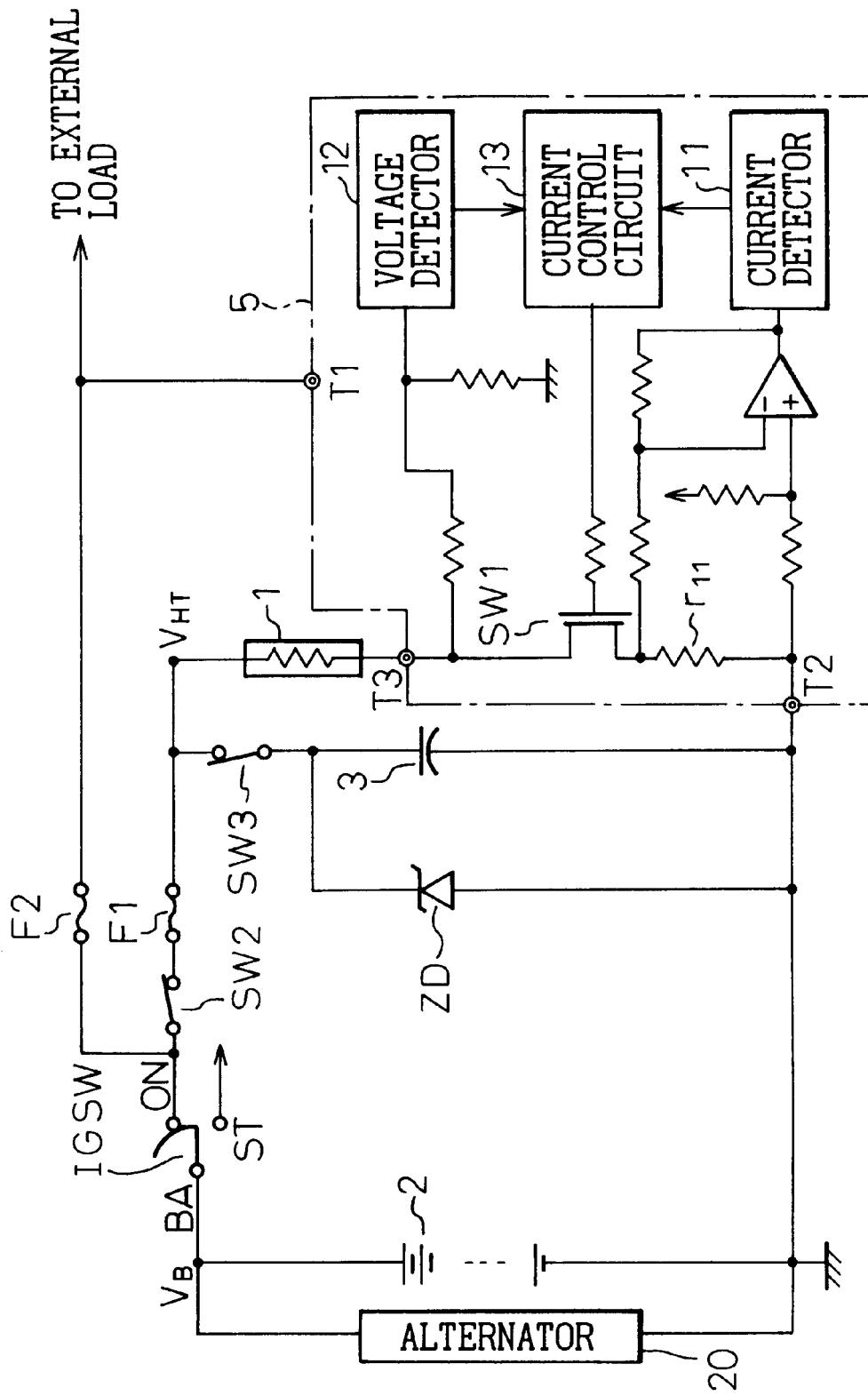
FIG. 4 is a diagram showing a configuration of a concrete example of the first aspect of the invention.
Figure 5A:
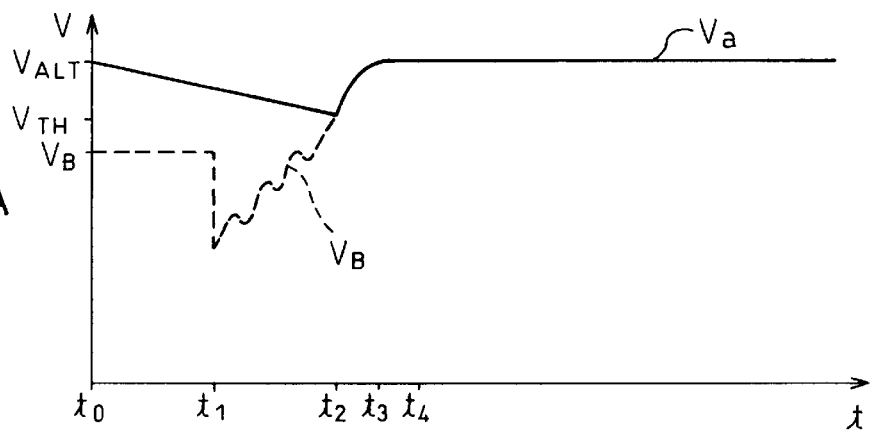
FIG. 5A is a time chart of the voltage applied to the heater according to a first control method in a concrete example of the first aspect of the invention.
Figure 5B:
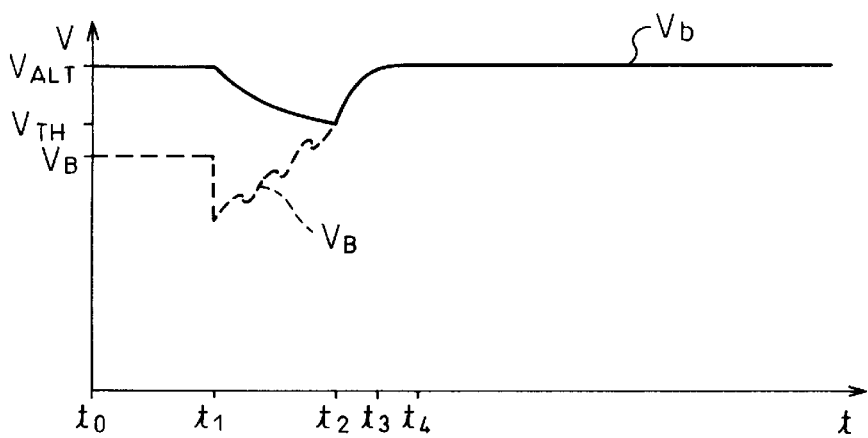
FIG. 5B is a time chart of the voltage applied to the heater according to a second control method in a concrete example of the first aspect of the invention.
Figure 5C:
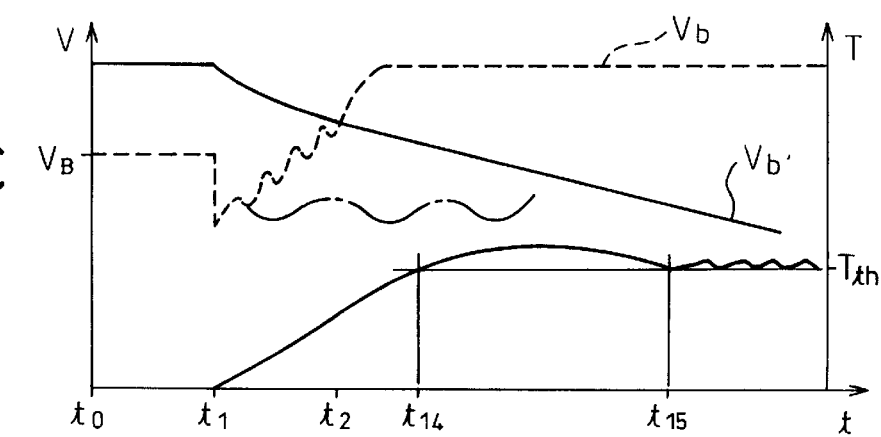
FIG. 5C is a time chart of the voltage applied to the heater according to a third control method in a concrete example of the first aspect of the invention.

FIG. 4 is a diagram showing a configuration of a concrete example according to the first aspect of the invention, FIG. 5A is a time chart of the heater voltage according to a first control method, FIG. 5B is a time chart of the heater voltage according to a second control method, and FIG. 5C is a time chart of the heater voltage according to a third control method. In the first control method, the heater is supplied with a current from the time point when an ignition switch is turned on. In the second control method, on the other hand, the heater is supplied with a current when the ignition switch is turned to the starter position. The third control method is similar to the second control method except that the current to the heater is inhibited when the heater temperature exceeds a predetermined level. As shown in FIG. 4, the heater 1 is heated by the power supplied from a power supply including a battery 2 and an alternator 20 thereby to activate an air-fuel ratio sensor (not shown). The current to the heater 1 is supplied or cut off by opening or closing a first switch SW1. The switch SW1 is made of an FET, for example, and is arranged in a control means 5 for controlling the current supplied to the heater 1. An external terminal T1 of the control means 5 is connected to the positive electrode of the battery 2 through an ignition switch IGSW and a fuse F2. An external terminal T2 is grounded, and an external T3 is connected to an end of the heater 1.

When the ignition switch IGSW is turned on, the voltage $V_B$ across the battery 2 is applied to the heater 1 through a second switch SW2 and the fuse F1. After that, when the control means 5 turns on the switch SW1, a current flows in the heater 1. The current flowing in the heater 1 is detected by a current detection circuit 11 based on the voltage across a current detecting resistor $r_{11}$. The voltage applied to the heater 1, on the other hand, is determined by detecting the voltages of the external terminals T1 and T3 and by calculating the difference therebetween. The voltage of the external terminal T1, i.e., the voltage $V_B$ across the battery 2 is detected by an electronic control unit (ECU) not shown, and the voltage of the external terminal T3 is detected by a voltage detection circuit 12. The ECU includes a digital computer having a ROM (read-only memory), a RAM (random access memory), a backup RAM, a CPU (microprocessor), an input port and an output port interconnected by a bidirectional bus 21. The FET used as the switch SW1 is turned on and off by a current control circuit 13 connected to the output port of the ECU.

The above-mentioned concrete example according to the first aspect of the invention includes a capacitor circuit 3 having at least a capacitor. The capacitor is charged by the battery 2 and the alternator 20 connected in parallel to the battery 2 primarily while the engine is running. The electricity charged to the capacitor is discharged through the heater 1 when the engine starts. This capacitor is called an electric double layer capacitor small in size and large in capacitance, and is so structured as to store the charge between activated carbon constituting an electrode and an organic electrolyte (polycarbonate) with a rated voltage of 2.5 volts. Assuming that the battery voltage is 13 V, therefore, the capacitor circuit 3 preferably includes five or six capacitors in series. The positive electrode of the capacitor circuit 3 is connected to the junction point between the fuse F1 and the heater 1 through the third switch SW3, and the negative electrode thereof is grounded. The second switch SW2 can be replaced by a diode. When the switch SW2 is opened or when the diode reduces the voltage across the battery 2 below the charge voltage of the capacitor circuit 3 during the engine cranking, the reverse flow of the current from the capacitor circuit 3 to the battery 2 can be prevented. Also, the capacitor circuit 3 is connected in parallel to a zener diode ZD for protecting the capacitor against an overvoltage. The second switch SW2 is opened for preventing the voltage across the battery 2 from falling if power is supplied to the heater 1 from the battery 2 when the engine is started. The third switch SW3 is for preventing the capacitor from being charged or discharged when the capacitor circuit 3 is faulty. The second switch SW2 or the third switch SW3 is opened after the engine stops and is advantageously used for preventing the capacitor from being discharged. Now, the control operation of the current control circuit 13 will be explained below with reference to FIGS. 5A, 5B and 5C.

In FIGS. 5A, 5B and 5C, the abscissa represents the time and the ordinate the voltage applied to the heater. A curve $V_a$ indicates the change with time of the voltage applied to the heater according to the first control method in which the heater 1 is supplied with current as soon as the ignition switch IGSW is turned on. A curve $V_b$ indicates the change with time of the voltage applied to the heater according to the second control method in which the heater 1 is not supplied with a current when the ignition switch IGSW turned on but the heater 1 is supplied with a current when the ignition switch IGSW is switched to the starter. A curve $V_{b'}$, on the other hand, indicates the change with time of the voltage applied to the heater according to the third control method similar to the above-mentioned second control method except that the switch SW1 is operated in accordance with the heater temperature in such a manner as to maintain the air-fuel ratio sensor in active state in the case where the battery is degenerated.

First, the curve $V_a$ will be explained with reference to FIG. 5A. At time point $t_0$, when the ignition switch IGSW is turned on, a voltage $V_{ALT}$ higher than the voltage $V_B$ across the battery 2 is applied to the heater 1. At the same time, the heater 1 begins to be supplied with a current, and the electricity stored in the battery 2 and the capacitor circuit 3 is discharged to the heater 1. The voltage $V_{HT}$ applied to the heater 1 is equal to the voltage $V_{ALT}$, higher than the voltage $V_B$ across the battery 2, due to the fact that during time when the engine is stationary, the battery 21 is discharged and the voltage across it drops but the capacitor circuit 3 is not substantially discharged and therefore the capacitor circuit 3 holds the voltage charged by the maximum output voltage $V_{ALT}$ of the alternator while the engine is running. Also in the concrete examples described with reference to this and subsequent diagrams, the voltage $V_{HT}$ applied to the heater 1 at time point $t_0$ assumes a value equal to $V_{ALT}$.

Returning to the curve $V_a$, the voltage $V_{HT}$ applied to the heater 1 begins to drop gradually from time point $t_0$ due to the power consumption by the heater 1. In the case where the engine starts at time point $t_1$, i.e., in the case where the ignition switch IGSW is switched to position ST, within several seconds of normal time $t_0$, then the ECU begins to drive a starter motor not shown. The voltage $V_B$ across the battery 2 drops sharply due to the activation current of the starter motor. Once the starter motor is activated, however, the current consumed by the starter motor decreases. In this way, the alternator 20 generates power and starts to charge the battery 2 and the capacitors of the capacitor circuit 3 by the rotation of the starter motor when starting the engine and by the rotation of the engine after the engine starts. As a consequence, the voltage $V_B$ begins to increase gradually at time point $t_1$.

Since the second switch SW2 is open and the third switch SW3 is closed, the voltage $V_{HT}$ applied to the heater 1 as indicated by curve $V_a$ gradually drops from the maximum output voltage $V_{ALT}$ of the alternator higher than the voltage $V_B$ across the battery 2 due to the power consumption by the heater 1 during the time from $t_0$ to $t_2$. The voltage $V_B$ across the battery 2 that has increased as the result of charging thereof by the alternator 20 at and after time point $t_1$ passes the predetermined voltage $V_{TH}$, not affecting the engine cranking at time point $t_2$, and then reaches the maximum output voltage $V_{ALT}$ of the alternator 20. This time point $t_2$ may be considered the one when the engine has reached a predetermined speed. As described above, as compared with the conventional system in which power begins to be supplied to the heater 1 at the voltage across the battery 2 at time $t_2$, the first control method according to the first aspect of the invention is such that power begins to be supplied to the heater 1 at the voltage $V_{ALT}$ higher than $V_B$ by the capacitor 3 at time point $t_0$, and therefore an earlier activation of the air-fuel ratio sensor is made possible.

As the heater 1 is heated from time point $t_0$, the air-fuel ratio sensor element is activated at an early time, so that the heater temperature and the sensor element temperature increase early. Thus, after the alternator 20 generates the maximum output voltage $V_{ALT}$ at time point $t_3$, the sensor element reaches an activation temperature $T_{th}$ of, say, 650° C. indicating the active state thereof and measurement of the air-fuel ratio (A/F) becomes possible at time point $t_4$. At and after time point $t_4$, the temperature of the heater 1 is controlled in such a manner as to maintain the sensor element in an active state. This concrete example uses a method of controlling the power supplied to the heater based on a power map prepared according to the engine operating conditions. As an alternative, a method may be used in which the resistance value of the heater is measured and controlled at a constant level or in which the resistance value of the sensor element is measured and controlled at a constant level.

A method of controlling the power supplied to the heater according to this concrete example will be described below. In the first step, the resistance value of the heater 1 is calculated from the current flowing in the heater 1 detected by the current detection circuit 11 and the voltage applied to the heater 1 detected by the voltage detection circuit 12. In the second step, the temperature of the heater 1 proportional to the resistance value of thereof is detected from the calculated resistance value of the heater 1. In the third step, power is supplied to the heater 1 in such a way as to maintain the temperature of the heater 1 at a sufficiently high level to maintain the air-fuel ratio sensor in active state. Also, the power supplied to the heater 1 is controlled by turning on and off the switch SW1 in a predetermined duty cycle in accordance with the duty factor calculated based on the basic electric energy corresponding to the engine operating conditions.

Now, the curve $V_b$ will be explained with reference to FIG. 5B. At time $t_0$ when the ignition switch IGSW is turned on, the voltage $V_{ALT}$ higher than the voltage $V_B$ across the battery 2 is applied to the heater 1. As of this time point, the heater 1 is not yet supplied with current. Consequently, the voltage $V_{HT}$ applied to the heater 1 holds the level of the voltage $V_{ALT}$ as of time point $t_0$ until time point $t_1$. With the starting of the engine, i.e., when the ignition switch IGSW is turned to position ST at time point $t_1$, the ECU begins to drive the starter motor not shown. Thus the voltage $V_B$ across the battery 2 sharply drops due to the activation current of the starter motor. Once the starter motor is activated, however, the current consumed in the starter motor decreases. Thus the alternator 20 (not shown) generates power and starts to charge the battery 2 by the rotation of the starter motor when starting the engine and by the rotation of the engine after the engine starts. At time point $t_1$, therefore, the voltage $V_B$ across the battery 2 begins to gradually increase.

In view of the fact that the second switch SW2 remains open and the third switch SW3 remains closed before time point $t_2$, the voltage $V_{HT}$ applied to the heater 1 indicated by curve $V_b$ gradually declines from the output voltage $V_{ALT}$ of the alternator 20 higher than the voltage $V_B$ across the battery 2 due to the power consumption by the heater 1 during the time period from $t_0$ to $t_1$. At and after time point $t_2$, the voltage $V_B$ across the battery 2, that has thus far increased as the result of being charged by the alternator 20, passes the predetermined voltage $V_{TH}$ without affecting the engine cranking at time point $t_2$ and then reaches the maximum output voltage $V_{ALT}$ of the alternator 20. The operation at and after time point $t_2$ is similar to that shown in FIG. 5A and will not be described. In this way, although the heater 1 begins to be supplied with current at or after time point $t_2$ in the conventional system, the second control method according to the second aspect of the invention is such that the heater 1 begins to be supplied with current at time point $t_1$ and this makes it possible to activate the air-fuel ratio quickly. Also, in spite of the fact that the time required for activation of the air-fuel ratio sensor is longer than the time required in the case indicated by curve $V_a$, the smaller drop of the voltage $V_B$ across the battery 2 at the time $t_1$, when the cranking starts, can secure the startability of the engine.

In addition to the first control method or the second control method according to the first aspect of the invention described above, the switch SW1 can be controlled to close only when the cranking is stable in order to prevent the deterioration of the engine startability. Judgement as to whether the cranking is stable can be made by detecting the engine speed, the change in engine speed, the drop of voltage across the battery, the engine water temperature, etc. and by checking whether these values are within a specified reference.

Now, the curve $V_{b'}$ will be explained with reference to FIG. 5C. The third control method shown in FIG. 5C is similar to the second control method according to the first aspect of the invention, but represents a case in which the engine cranking is protracted due to the degeneration of the battery. The curve $V_{b'}$ shown in FIG. 5C, like the curve $V_b$ shown in FIG. 5B, indicates the change with time of the voltage applied to the heater 1 not supplied with current while the ignition switch IGSW remains on but supplied with current from the time when the ignition switch IGSW is turned to the starter. In the third control method, the switch SW1 is opened in the case where the voltage $V_B$ across the battery 2 fails to reach a predetermined value before time point $t_2$ in FIG. 5B after the cranking starts at time point $t_1$ and in the case where the air-fuel ratio sensor element reaches an activation temperature $T_{th}$ of, say, 650° C. indicating the active state thereof and the air-fuel ratio (A/F) becomes measurable at time point $t_{14}$. Subsequently, in order to maintain the active state of the air-fuel ratio sensor element, the heater temperature control is suspended, i.e., power stops being supplied to the heater by operating the switch SW1 based on the power map prepared in accordance with the engine operating conditions. The switch SW1 is closed again at or after time point $t_{15}$ when the temperature of the heater 1 calculated from the resistance value thereof drops to or below the predetermined level of 650° C., and thus the heater temperature is controlled. This process is repeated. The third control method can prevent the battery 2 from being excessively consumed by the temperature increase of the heater 1.

In the first aspect of the invention, it is also possible to detect the voltage $V_{HT}$ applied to the heater 1 when the switch SW2 is open and to determine a fault of the capacitor circuit 3 from the detected voltage. A fault of the capacitor circuit 3 can be indicated, for example, by turning on a display lamp.

The system according to this aspect of the invention can further comprise a third switch SW3 which is connected in series to the capacitor circuit 3 for supplying or cutting off the charging current or the discharging current of the capacitor circuit 3 after a fault in the capacitor circuit is detected.

When a fault is detected, the switch SW1 is controlled to close at the end of the engine cranking while at the same time controlling the switch SW3 to turn it to normally open state thereby to secure the reliability of the system.

As described above, the heater control system for an air-fuel ratio sensor of an internal combustion engine according to the first aspect of the invention comprises a capacitor circuit isolated from the battery and alternator at the time of starting the engine and connected in parallel to the battery and the alternator while the engine is running, wherein power is supplied to the heater at the time of starting the engine from the capacitor circuit charged at the maximum output voltage of the alternator higher than the battery voltage. As a result, an earlier activation of the air-fuel ratio sensor is realized at the time of starting the engine, while at the same time suppressing the deterioration of the exhaust emission at an early time. Also, the capacitor circuit is isolated from the battery and the alternator, the starter motor is activated by use of the power of the battery when the engine starts, and the heater temperature is increased using the capacitor circuit but not the battery. Therefore, the engine startability can be secured while at the same time activating the air-fuel ratio sensor quickly without decreasing the battery voltage.

The second aspect of the present invention will be described in-detail below.

Figure 6:
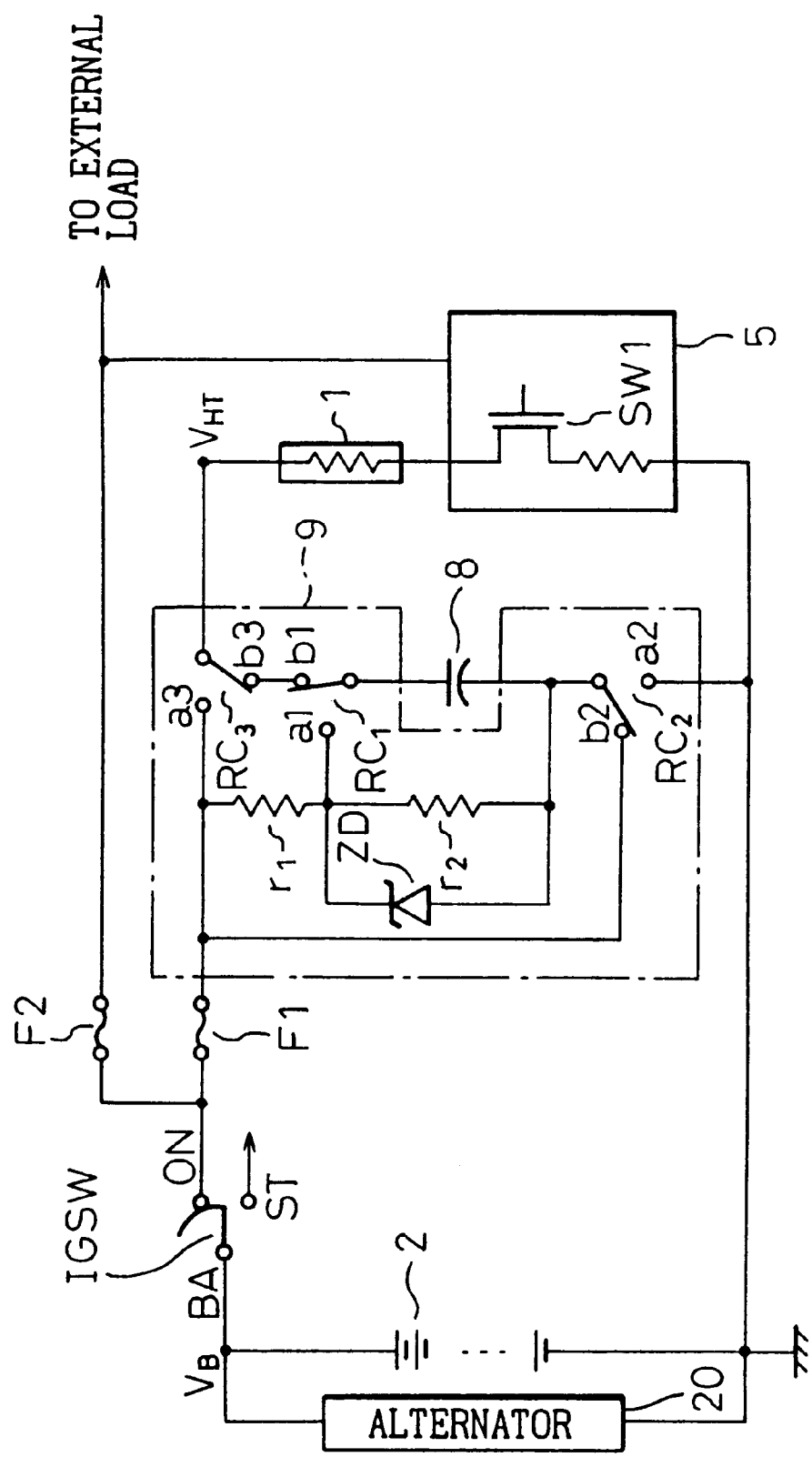
FIG. 6 is a diagram showing a configuration of a first concrete example of the second aspect of the invention.
Figure 7A:
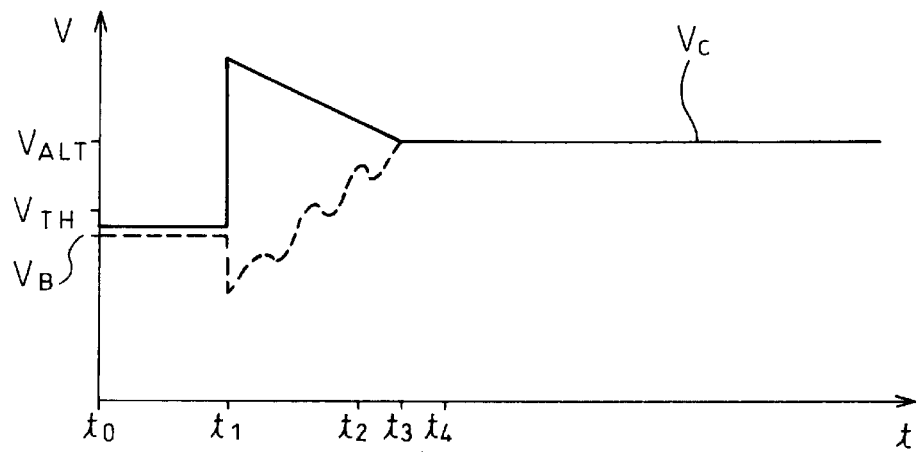
FIG. 7A is a time chart of the voltage applied to the heater according to the first control method in a first concrete example of the second aspect of the invention.
Figure 7B:
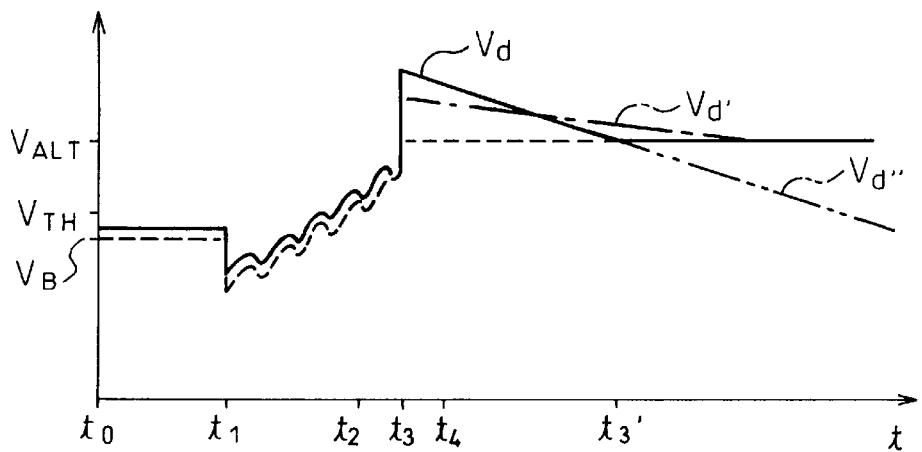
FIG. 7B is a time chart of the voltage applied to the heater according to the second control method in a first concrete example of the second aspect of the invention.

FIG. 6 is a diagram showing a configuration of a first concrete example of the second aspect of the invention, FIG. 7A is a time chart of the voltage applied to the heater by the first control method according to the first concrete example of the second aspect of the invention, and FIG. 7B is a time chart of the voltage applied to the heater by the second control method. According to the first control method, the heater is supplied with power from the time point when the ignition switch IGSW is turned to the starter position. In the second control method, on the other hand, the heater begins to be supplied with current when the voltage across the battery reaches a level not affecting the engine cranking after the ignition switch IGSW is turned to the starter position.

In FIG. 6, the control means 5, though shown in a simplistic form, is similar, in the details thereof, to the corresponding one shown in FIG. 4. The configuration of the first concrete example according to the second aspect of the invention will be explained in comparison with the configuration of a concrete example of the first aspect of the invention shown in FIG. 4. As seen from these diagrams, the difference in configuration between the concrete example of the first aspect and the first concrete example of the first aspect of the invention lies in that the second switch SW2, the third switch SW3 and the capacitor circuit 3 in the concrete example of the first aspect of the invention are removed, and are replaced by the capacitor circuit 8 and the charge-discharge switching means 9 and in that the control means 5 has a different control method. The remaining portions of the configuration are substantially identical to those of the system according to the second concrete example.

The capacitor circuit 8 of the first concrete example according to the second aspect of the invention shown in FIG. 6 includes a capacitor. The capacitor circuit 8 is different from the capacitor circuit 3 of the concrete example according to the first aspect of the invention in that the capacitor 8 is charged at a lower voltage than the capacitor circuit 3 of the concrete example according to the first aspect while the engine is running after being started. Specifically, the capacitor circuit 8 is charged at the maximum output voltage $V_{ALT}$ of the alternator 20, divided by the resistors $r_1$, $r_2$, i.e., at a voltage $r_2V_{ALT}/(r_1+r_2)$, a zener diode ZD for protecting the capacitors against an overvoltage is connected in parallel, and the circuit configuration is switched by the charge-discharge switching means 9 at the time of charge or discharge. At the time of charging, the charge-discharge switching means 9 excites all the relays $R_1$, $R_2$ and $R_3$ not shown, closes the (normally-open) contact points a1 to a3 of the corresponding relay contacts $RC_1$, $RC_2$ and $RC_3$ and opens the (normally-closed) contact points b1 to b3. At the time of discharge, on the other hand, the relays $R_1$, $R_2$ and $R_3$ are all deenergized to open the contact points a1 to a3 of the corresponding relay contacts $RC_1$, $RC_2$ and $RC_3$ while closing the contact points b1 to b3. Now, the control of the current control circuit 13 will be explained with reference to FIGS. 7A and 7B.

In FIGS. 7A and 7B, the abscissa represents the time and the ordinate the voltage applied to the heater. A curve $V_c$ represents the change with time of the voltage $V_{HT}$ applied to the heater 1 by the first control method, and a curve $V_d$ indicates the change with time of the voltage $V_{HT}$ applied to the heater 1 by the second control method. First, the curve $V_c$ will be explained with reference to FIG. 7A. At time point $t_0$ when the ignition switch IGSW is turned on, the voltage $r_2V_B/(r_1+r_2)$ obtained by dividing the voltage $V_B$ across the battery 2 by the resistors $r_1$, $r_2$ is applied to the capacitor circuit 8, while the voltage $V_B$ across the battery is applied to the heater 1. As of this time point, however, the heater is not supplied with any current, and therefore the voltage $V_{HT}$ applied to the heater 1 is held at the voltage $V_B$ associated with the time point $t_0$. When the engine starts, i.e., when the ignition switch IGSW is turned to position ST at time point $t_1$, the ECU starts driving the starter motor not shown. At this time point $t_1$, the relays $R_1$, $R_2$ and $R_3$ are deenergized, and the charge-discharge switching circuit 9 is turned from charge to discharge mode. Then, at time point $t_1$, the heater 1 is impressed with the voltage $V_B$ across the battery 2 plus the charge voltage of the capacitor circuit 8. In view of the fact that the maximum output voltage $V_{ALT}$ of the alternator 20 is applied to the capacitor circuit 8 while the engine is running, the charge voltage of the capacitor circuit 8 equal to the voltage $V_{ALT}$ divided by the resistors $r_1$, $r_2$, i.e., a voltage $r_2V_{ALT}/(r_1+r_2)$ is applied to the capacitors and held even after the engine stops.

Since the starter motor begins to be driven at time point $t_1$, however, the activation current of the starter motor causes the voltage $V_B$ across the battery 2 to decline sharply as shown by dashed line in FIG. 7A. After activation of the starter motor, however, less current is consumed in the starter motor. The alternator 20 (not shown) is caused to generate power and begins to charge the battery 2 by the rotation of the starter motor when starting the engine and by the rotation of the engine after the engine starts. Consequently, the voltage $V_B$ across the battery 2 steadily increases at and after time $t_1$, and after passing the predetermined voltage $V_{TH}$, not affecting the engine cranking, at time point $t_2$, soon reaches the maximum output voltage $V_{ALT}$ of the alternator 20 at time point $t_3$. The voltage $V_{HT}$ applied to the heater 1 shown by solid line $V_c$ in FIG. 7A, on the other hand, assumes $V_B+r_2V_{ALT}/(r_1+r_2)$ at time point $t_1$. At and after time point $t_1$, however, the electricity charged in the capacitor circuit 8 gradually decreases due to the power consumption by the heater 1, and soon after that, the applied voltage $V_{HT}$ gradually drops until the relays $R_1$, $R_2$, $R_3$ are excited at time point $t_3$ when the electricity charged in the capacitor circuit 8 is discharged by the power consumption in the heater 1. At time point $t_3$ when the voltage $T_{HT}$ decreases to the maximum output voltage $V_{ALT}$ of the alternator 20 soon after time point $t_1$, the relays $R_1$, $R_2$, $R_3$ are excited, so that the charge-discharge switching circuit 9 is switched from discharge to charge mode, while at the same time supplying power to the heater 1 from the battery 2 and the alternator 20. As described above, according to the prior art, power is supplied to the heater 1 at the voltage of the battery 2 at or after time point $t_2$. In the first control method according to a first concrete example of the second aspect of the invention, on the other hand, power begins to be supplied to the heater 1 at time point $t_1$ and the heater 1 is impressed with a high voltage constituting the sum of the voltage $V_B$ across the battery 2 and the voltage $r_2V_{ALT}/(r_1+r_2)$ charged to the capacitor 8. The air-fuel ratio sensor thus can be activated at an early time.

At time point $t_1$ when the heater 1 begins to be heated, the air-fuel sensor element is activated, and the temperature of the heater and the sensor element increases until the sensor element reaches an activation temperature $T_{th}$ of, say, 650° C. indicating the active state of the sensor element, thus making it possible to measure the air-fuel ratio (A/F). At and after time point $t_4$, the temperature of the heater 1 is controlled in such a manner as to maintain the active state of the sensor element. According to this concrete example, a method is employed in which the power supplied to the heater is controlled based on a power map prepared in accordance with the engine operating conditions. As an alternative, a method can be used in which the resistance value of the heater is measured and controlled at a constant value, or in which the resistance value of the sensor element is measured and maintained at a constant level. The method of controlling the power supplied to the heater for maintaining the air-fuel ratio sensor in active state according to the first concrete example of the second aspect of the invention is identical to that according to a concrete example of the first aspect of the invention, and therefore will not be described further.

Now, the curve $V_d$ will be explained with reference to FIG. 7B. At time point $t_0$ when the ignition switch IGSW is turned on, a voltage $r_2V_B/(r_1+r_2)$ obtained by dividing the voltage $V_B$ across the battery 2 by the resistors $r_1$, $r_2$, is applied to the capacitor circuit 8. As of this time point, the heater 1 is not yet supplied with current, and therefore the voltage $V_{HT}$ applied to the heater 1 holds the same voltage as the voltage $V_B$ across the battery 2. At time point $t_1$ when the engine starts, i.e., when the ignition switch IGSW is turned to position ST, the ECU begins to drive the starter motor not shown, and therefore the voltage $V_B$ across the battery 2 sharply drops due to the activation current of the starter motor. Once the starter motor is activated, however, the current consumed in the starter motor is reduced, so that the alternator 20 (not shown) generates power and begins to charge the battery 2 by the rotation of the starter motor when the engine starts and by the rotation of the engine after the engine starts. As a result, the voltage $V_B$ across the battery 2 begins to gradually increase at time point $t_1$, and after passing the predetermined voltage $V_{TH}$, not affecting the engine cranking, at time point $t_2$, reaches the maximum output voltage $V_{ALT}$ of the alternator 20.

Assume that the relays $R_1$, $R_2$ and $R_3$ are deenergized and the charge-discharge switching circuit 9 is turned from charge to discharge mode at this time point $t_3$. Then, the heater 1 is impressed with the voltage $V_B$ across the battery 2 plus the voltage $r_2V_{ALT}/(r_1+r_2)$ charged to the capacitor circuit 8 while the engine is running. At and after time point $t_3$, the voltage charged to the capacitor circuit 8 is discharged due to the power consumption by the heater 1, and the voltage $V_{HT}$ applied to the heater 1 gradually declines. The voltage $V_{HT}$ thus drops to the maximum output voltage $V_{ALT}$ of the alternator 20 at time point $t_3'$, when the relays $R_1$, $R_2$, $R_3$ are excited to switch the charge-discharge switching circuit 9 from discharge to charge mode while at the same time supplying power to the heater 1 from the battery 2 and the alternator 20. In this way, unlike the prior art in which power begins to be supplied to the heater 1 at the voltage across the battery 2 at and after time point $t_2$, the second control method according to the second aspect of the invention is such that although power begins to be supplied to the heater 1 at time point $t_3$, the heater 1 is impressed with a voltage equal to the sum of $r_2V_{ALT}/(r_1+r_2)$ charged to the capacitor circuit 8 and the voltage $V_B$ across the battery 2, thereby making possible an earlier activation of the air-fuel ratio sensor. At and after time point $t_3'$ shown in FIG. 7B, the operation is identical to that shown in FIG. 7A and will not be described again.

Also, according to the second aspect of the invention, the voltage applied to the heater 1 is detected each time the charge-discharge switching circuit 9 is operated to switch the capacitor circuit 8 to charge or discharge mode, and the resulting voltage difference is used to judge that the capacitor circuit 8 is faulty in the case where the voltage in the beginning of charging fails to increase over the voltage during the charging by an amount equivalent to the voltage charged to the capacitor circuit 8. In such a case, a display lamp, for example, is lit to indicate a fault in the capacitor circuit.

Further, in the case where the capacitor circuit 8 is judged as faulty, the switch SW1 is controlled to close at the end of engine cranking and at least one of the terminals of the capacitor circuit 8 connected to the charged-discharge switching circuit 9 is controlled to normally open state, thereby improving the system reliability. For at least one of the terminals of the capacitor circuit 8 to be switched to normally open state, a contact $RC_n$ of a new relay $R_n$ (not shown) is inserted between the terminal of the positive electrode of the capacitor circuit 8 and the a common terminal cl of the contact $RC_1$ of the relay $R_1$. This contact $RC_n$ is set to normally closed state and is opened when a fault in the capacitor circuit 8 is detected. Now, with reference to the capacitor circuit 8 according to the first concrete example of the first aspect of the invention shown in FIG. 6, an explanation will be made about a second concrete example (FIG. 8) in which a single capacitor is replaced by a plurality of capacitors in series or parallel, a third concrete example (FIG. 9) in which a single capacitor is replaced by a plurality of capacitors connected in series, and a fourth concrete example (FIG. 10) in which a single capacitor is replaced by a plurality of capacitors capable of switching the discharge voltage pattern between a plurality of modes. In these second to fourth concrete examples, the configuration except for the capacitor circuit 8 and the charge-discharge circuit 9 is substantially identical to that of the first concrete example shown in FIG. 6, and therefore will not be described again.

Figure 8:
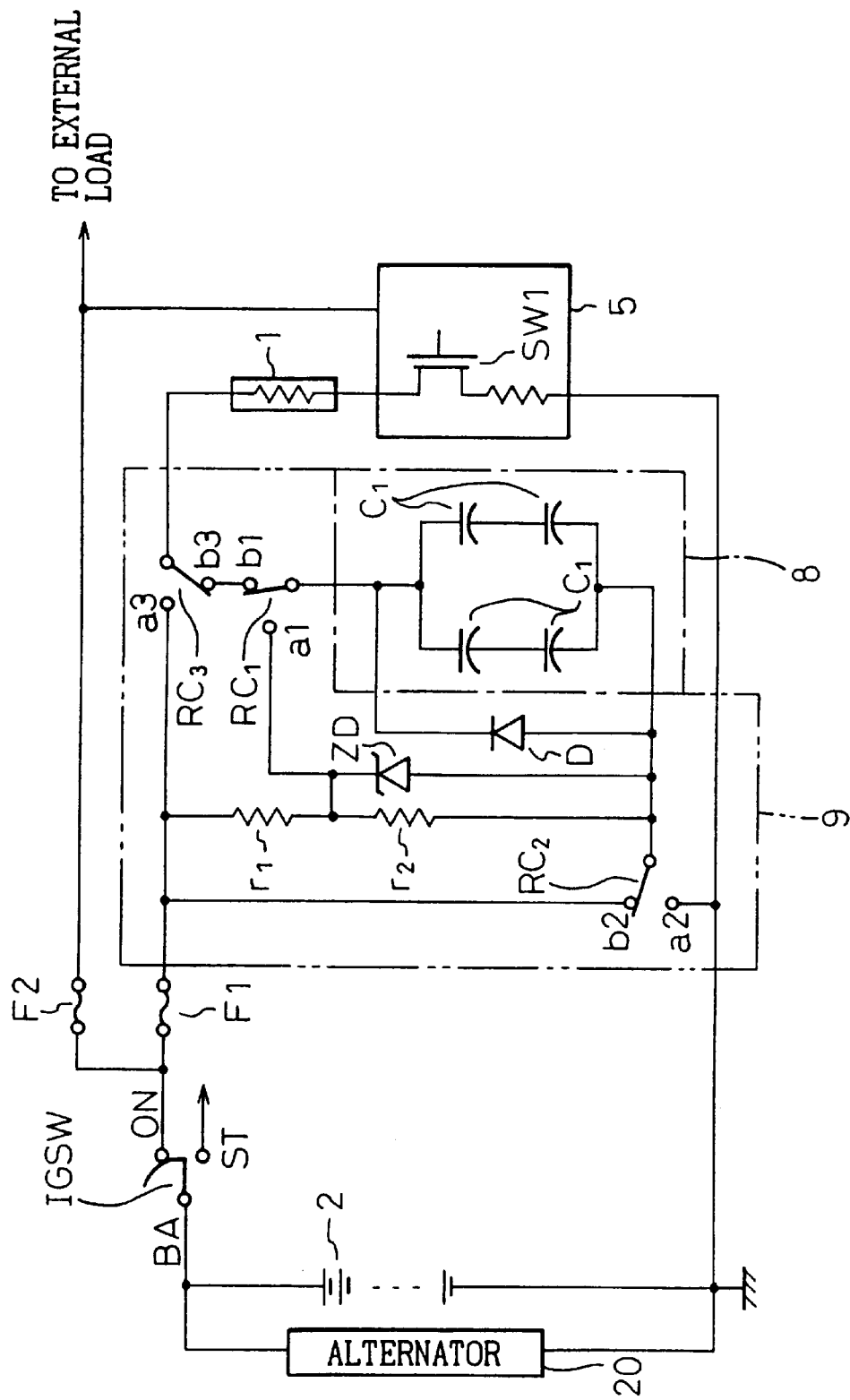
FIG. 8 is a diagram showing a configuration of a second concrete example of the second aspect of the invention.

FIG. 8 is a diagram showing a configuration of the second concrete example according to the second aspect of the invention. The capacitor circuit 8 shown in FIG. 8 includes four capacitors $C_1$ of the same capacitance, each two of which are connected in series and in parallel. The charge-discharge switching means 9 includes contacts $RC_1$, $RC_2$, $RC_3$ of the relays $R_1$, $R_2$, $R_3$, respectively, (not shown), a zener diode ZD for protecting the capacitors $C_1$ against an overvoltage at the time of charging, a bypass diode-D for supplying a current from the battery 2 to the heater 1 when the voltage of the positive electrode of the capacitors C1 drops to the neighborhood of the voltage of the negative electrode thereof at the time of discharge, and voltage-dividing resistors $r_1$, $r_2$ for setting a charge voltage for the capacitor circuit 8. The bypass diode D is useful for supplying power to the heater 1 when a fault occurs in the capacitor circuit 8. The ECU excites all the relays $R_1$ to $R_3$ and closes the contact points a1 to a3 of all the relay contacts $RC_1$ to $RC_3$ of the relays $R_1$ to $R_3$ at the time of charging the capacitors $C_1$.

All the relays $R_1$ to $R_3$, on the other hand, are deenergized thereby to close the contact points a1 to a3 of all the relay contacts $RC_1$ to $RC_3$ of the relays $R_1$ to $R_3$ at the time of discharging the capacitors $C_1$. The internal resistance of the capacitor circuit 8 as a whole is given as $r_1$ on the assumption that the resistance value of the internal resistor of each capacitor $C_1$ is $r_1$. The internal resistance, therefore, is smaller than when a plurality of capacitors $C_1$ are connected in series. Suppose that four capacitors $C_1$ each having an internal resistance $r_1$ are connected in series. The internal resistance of the capacitor circuit 8 as a whole is $4r_1$, which is four times as large as the internal resistance $r_1$ of the capacitor circuit 8 including parallel-connected capacitors shown in FIG. 8. As a result, with the capacitor circuit 8 having a plurality of capacitors, the attenuation gradient of the voltage applied to the heater 1 at the time of discharge can be more gentle for a parallel connection than for a series connection. The voltage $V_{HT}$ applied to the heater 1 when using this capacitor circuit faithfully follows the curve $V_d$ indicated by solid line in FIG. 7B from time point $t_0$ to $t_3$. At time point $t_3$, however, a voltage calculated by the equation $$V_B + r_2 \times V_{ALT}/(r_1 + r_2)$$

is applied to the heater 1. At and after time point $t_3$, the applied voltage $V_{HT}$ changes according to the curve $V_{d'}$ indicated by one-dot chain, and is finally held constant at the maximum output voltage $V_{ALT}$ of the alternator 20.

Figure 9:
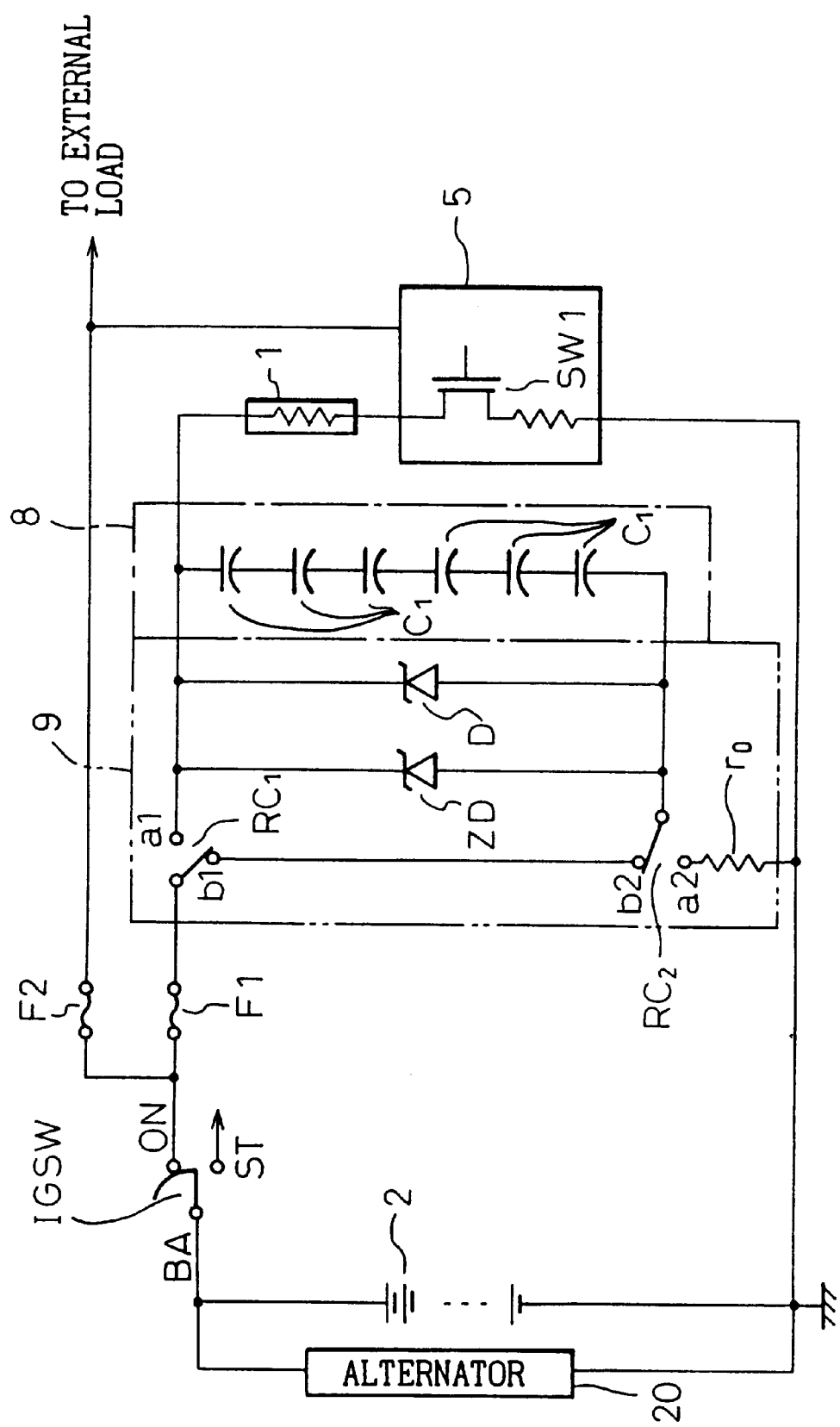
FIG. 9 is a diagram showing a configuration of a third concrete example of the second aspect of the invention.

FIG. 9 is a diagram showing a configuration of a third concrete example according to the second aspect of the invention. The capacitor circuit 8 shown in FIG. 9 includes six capacitors $C_1$ of the same capacitance connected in series. The charge-discharge switching means 9 includes contacts $RC_1$, $RC_2$ of the relays $R_1$, $R_2$ not shown, respectively, a zener diode ZD for protecting the capacitors $C_1$ against an overvoltage at the time of charging, a bypass diode D for supplying current from the battery 2 to the heater 1 when the positive electrode voltage of the capacitors $C_1$ declines to the neighborhood of the negative electrode voltage thereof at the time of discharging, and a resistor $r_0$ connected between the contact point a2 of the contact $RC_2$ and the ground terminal of the battery 2 and the switch SW1 for the heater 1. The ECU excites both the relays $R_1$ and $R_2$ and closes the contact points a1 and a2 of the two relay contacts $RC_1$, $RC_2$ at the time of charging the capacitors $C_1$, while it deenergizes both the relays $R_1$, $R_2$ and closes the contact points b1 and b2 of the two relay contacts $RC_1$, $RC_2$ at the time of discharging the capacitors $C_1$. The internal resistance of the capacitor circuit 8 as a whole is given as $6r_1'$ on the assumption that the internal resistance of each capacitor $C_1$ is $r_1'$. As compared with the series and parallel connections of the capacitors $C_1$ shown in FIG. 8, the gradient of attenuation of the voltage applied to the heater 1 becomes more sharp at the time of discharging. Nevertheless, it is possible to eliminate the voltage-dividing resistors $r_1$, $r_2$ for setting a charge voltage for the capacitor circuit 8.

The voltage $V_{HT}$ applied to the heater 1 when using this capacitor circuit exactly follows the curve $V_d$ indicated by solid line in FIG. 7B from time point $t_0$ to $t_3$. At and after time point $t_3$, however, the curve $V_{d'}$ though coincident with curve $V_d$ in the presence of the bypass diode D, changes to follow a curve $V_{d''}$ indicated by two-dot chain in the absence of the bypass diode D. Also, the resistor $r_0$ suppresses the repetition of charge and discharge of the capacitors against variations of the source voltage due to the battery 2 and the alternator 20. At the same time, the resistor $r_0$ is adapted to absorb any voltage which may be applied to the capacitors and which is higher than the zener voltage of the zener diode ZD for protecting the capacitors against an overvoltage.

Figure 10:
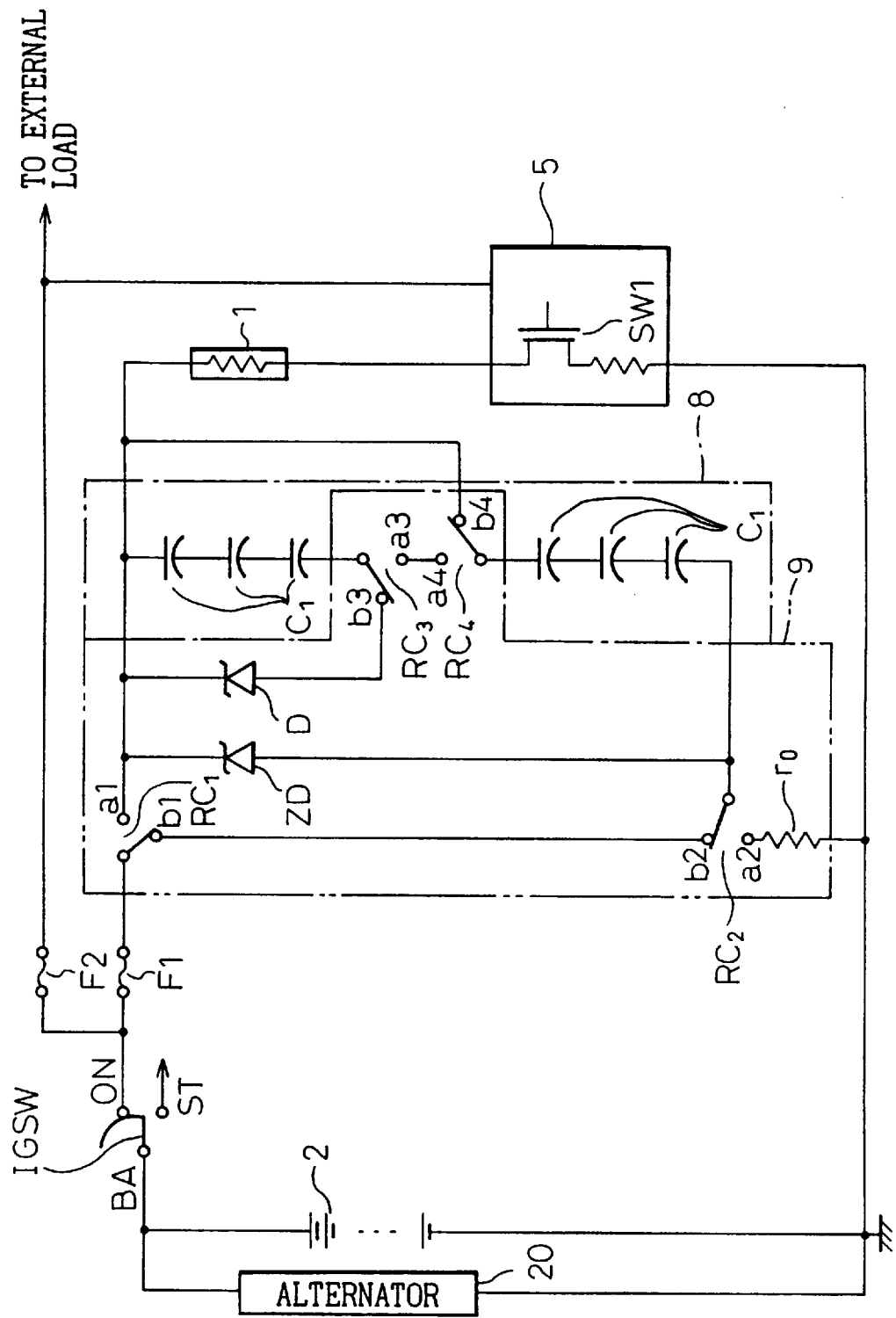
FIG. 10 is a diagram showing a configuration of a fourth concrete example of the second aspect of the invention.

FIG. 10 is a diagram showing a configuration of a fourth concrete example according to the second aspect of the invention. The fourth concrete example according to the second aspect of the invention shown in FIG. 10 is different from the capacitor circuit 8 and the charge-discharge switching means 9 in the fourth concrete example of the second aspect shown in FIG. 9, in that each three of six capacitors $C_1$ of the same capacitance are connected in series to form a capacitor group, in that these capacitor groups are connected to each other through the contact $RC_3$, $RC_4$ of the relays $R_3$, $R_4$, respectively, and in that the control means 5 is operated differently for control. Therefore, only these points will be described below. When the relays $R_3$, $R_4$ are excited, the contact points a3 and a4 of the relay contacts $RC_3$, $RC_4$ close, so that the two capacitor groups are connected in series to each other, while when the relays $R_3$, $R_4$ are deenergized, the contact points b3 and b4 of the relay contacts $RC_3$, $RC_4$ are closed so that the two capacitor groups are connected in parallel to each other.

Explanation will be about the operation of the capacitor circuit 8 and the charge-discharge switching means 9 shown in FIG. 10. After the engine starts, the ignition switch IGSW is in an on state, and therefore all the relays $R_1$ to $R_4$ are excited and the contact points a1 to a4 of the relay contacts $RC_1$ to $RC_4$ are closed. The six capacitors $C_1$, therefore, are connected in series to each other and are charged by the voltage generated by the alternator 20. In the process, the zener diode ZD protects the capacitors $C_1$ to $C_6$ against an overvoltage, and the resistor $r_0$ adjusts the time constant of the charge and discharge operation of the capacitors $C_1$ to $C_6$ and absorbs a voltage, if any, higher than the zener voltage which may be applied to the capacitors. When the engine is stationary, on the other hand, the ignition switch IGSW is in off state, so that the relays $R_1$ to $R_4$ are deenergized thereby to suppress the discharge of the capacitors $C_1$ to $C_6$. In the fourth concrete example of the second aspect of the invention, the relays $R_1$ to $R_4$ are deenergized from time point $t_1$ when the ignition switch IGSW is turned on and switched to the starter position to time point $t_2$ when the engine reaches the cranking speed. During this period, the two capacitor groups are connected in parallel to each other, so that the charge voltage of the capacitors is added to the voltage across the battery 2 and the resulting voltage is applied to the heater 1 thereby to heat the air-fuel ratio sensor quickly. Now, the change with time of the voltage applied to the heater 1 from the time point when the engine starts to a time point after the engine starts will be explained with reference to FIG. 11.

Figures 11, 12:
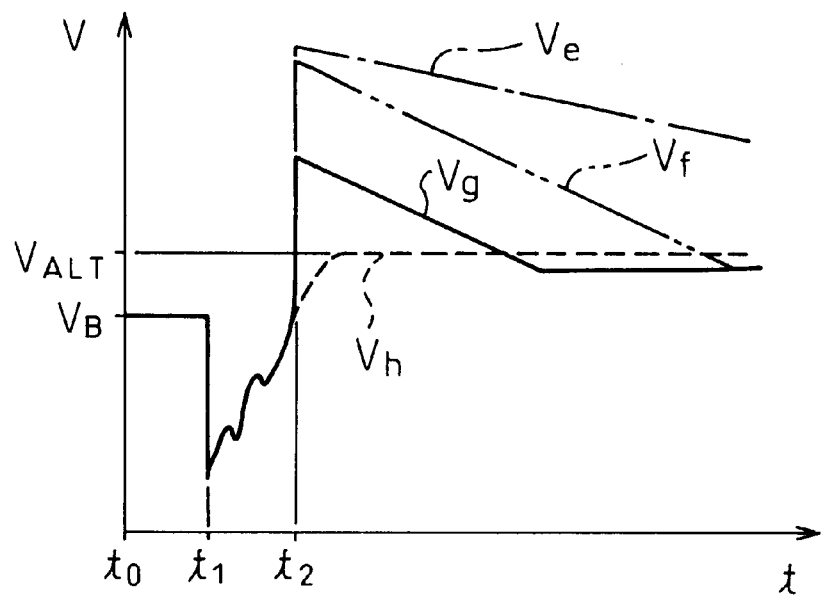
FIG. 11 is a time chart of the voltage applied to the heater according to a fourth concrete example of the second aspect of the invention.
FIG. 12 is a diagram showing a relay switching mode.

FIG. 11 is a time chart of the voltage applied to the heater in the fourth concrete example according to the second aspect of the invention, and FIG. 12 is a diagram showing the relay switching modes. In FIG. 11, the abscissa represents the time, and the ordinate the voltage applied to the heater 1. Assume the case in which the ignition switch IGSW is turned on at time point $t_0$ and set to the starter position at time point $t_1$ for performing the engine cranking, and in which the relays $R_3$ and $R_4$ are switched to one of the modes 1 to 4 shown in FIG. 12 at time point $t_2$ when the engine reaches a predetermined speed. In the waveform of the voltage applied to the heater in such a case, the mode 1 is indicated by a one-dot chain curve $V_e$, the mode 4 is indicated by a two-dot chain curve $V_f$, and the modes 2 and 3 are indicated by solid curve $V_g$. Also, an example of supplying power to the heater 1 directly from the battery 2 without using any conventional capacitor circuit is shown in dashed-line curve $V_h$. In this way, a discharge voltage pattern corresponding to each mode is obtained.

Figure 13A:
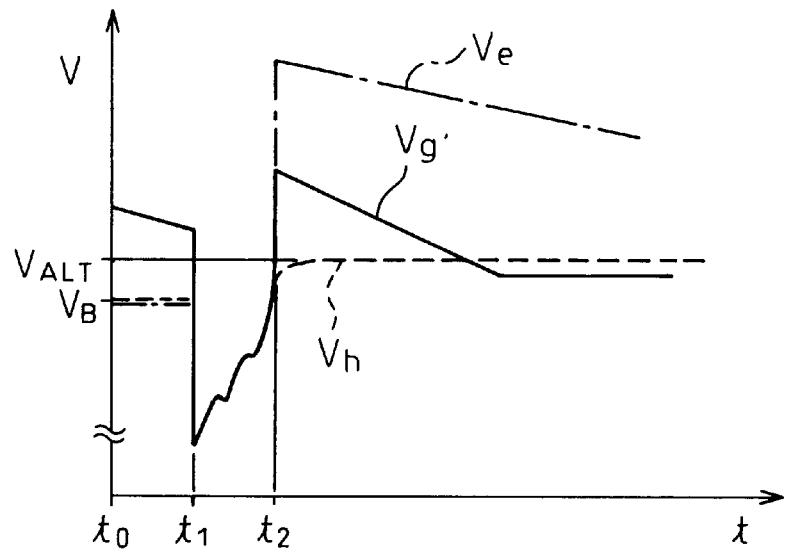
FIG. 13A is a time chart of the voltage applied to the heater according to a fifth concrete example of the second aspect of the invention.
Figure 13B:
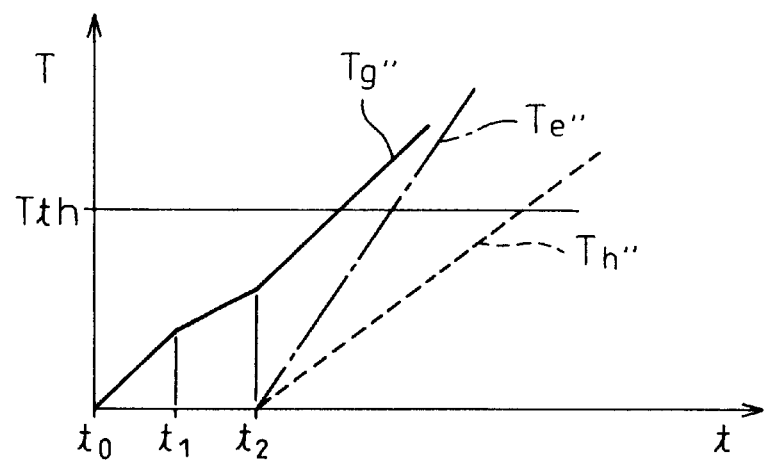
FIG. 13B is a time chart for the temperature of an air-fuel ratio sensor element according to a fifth concrete example of the second aspect of the invention.

FIG. 13A is a time chart of the voltage applied to the heater in the fifth concrete example according to the second aspect of the invention, and FIG. 13B is a time chart of the temperature of the air-fuel ratio sensor element. The fifth concrete example of the second aspect is different from the fourth concrete example of the second aspect shown in FIG. 10 in the control method of the control means 5. Therefore, only this point will be explained below. At time point $t_0$ when the ignition switch IGSW is turned on, the relays $R_3$, $R_4$ are switched to mode 2 shown in the table of FIG. 12 and the electricity charged in the capacitor group including the capacitors $C_1$ to $C_3$ is supplied to the heater 1. The ignition switch IGSW is set to the starter position at time point $t_1$ to start cranking. Until time point $t_2$ when the engine reaches a predetermined speed, the first switch SW1 is kept open while suspending energization of the heater 1 with the relays kept in mode 2. At time point $t_2$, the relays $R_3$, $R_4$ are switched to mode 3 as shown in the table of FIG. 12.

The waveform of the voltage applied to the heater 1 associated with the above-mentioned control operation is shown by solid curve $V_{g'}$ in the time chart of FIG. 13A, in which curves $V_e$, $V_h$ in FIG. 11 are also plotted in superposition. Modes 2 and 3 to which the relays are switched can be reversed in order. In FIG. 13B, the temperature change of the air-fuel ratio sensor element under the above-mentioned control in the fifth concrete example of the second aspect is shown by solid curve $T_{g''}$. Also, one-dot chain curve $T_{e''}$ indicates the temperature change of the air-fuel ratio sensor element in the case where the relays are set to mode 1 at time point $t_2$ in the fourth concrete example of the second aspect of the invention, and dashed-line curve $T_{h''}$ represents the case in which power is supplied to the heater directly from the battery without using the conventional capacitor circuit. These curves are shown superimposed on the time chart of FIG. 13B. It can be seen from FIG. 13B that, as compared with the prior art, the air-fuel ratio sensor element can be activated quickly in mode 1 of the fourth concrete example, and that the air-fuel ratio sensor element can be activated earlier in the fifth concrete example than in the fourth concrete example.

As described above, with the heater control system for an air-fuel ratio sensor of an internal combustion engine according to the second aspect of the invention, a power supply including a battery and an alternator is connected in series to a capacitor circuit charged beforehand while the engine is running, and power is supplied to the heater at a high voltage produced by superimposing the charge voltage of the capacitor circuit on the source voltage when starting the engine. Consequently, an early activation of the air-fuel ratio sensor can be realized at the time of starting the engine, while suppressing the deterioration of the exhaust emission.

The third concrete example will be described in detail below.

Figure 14:
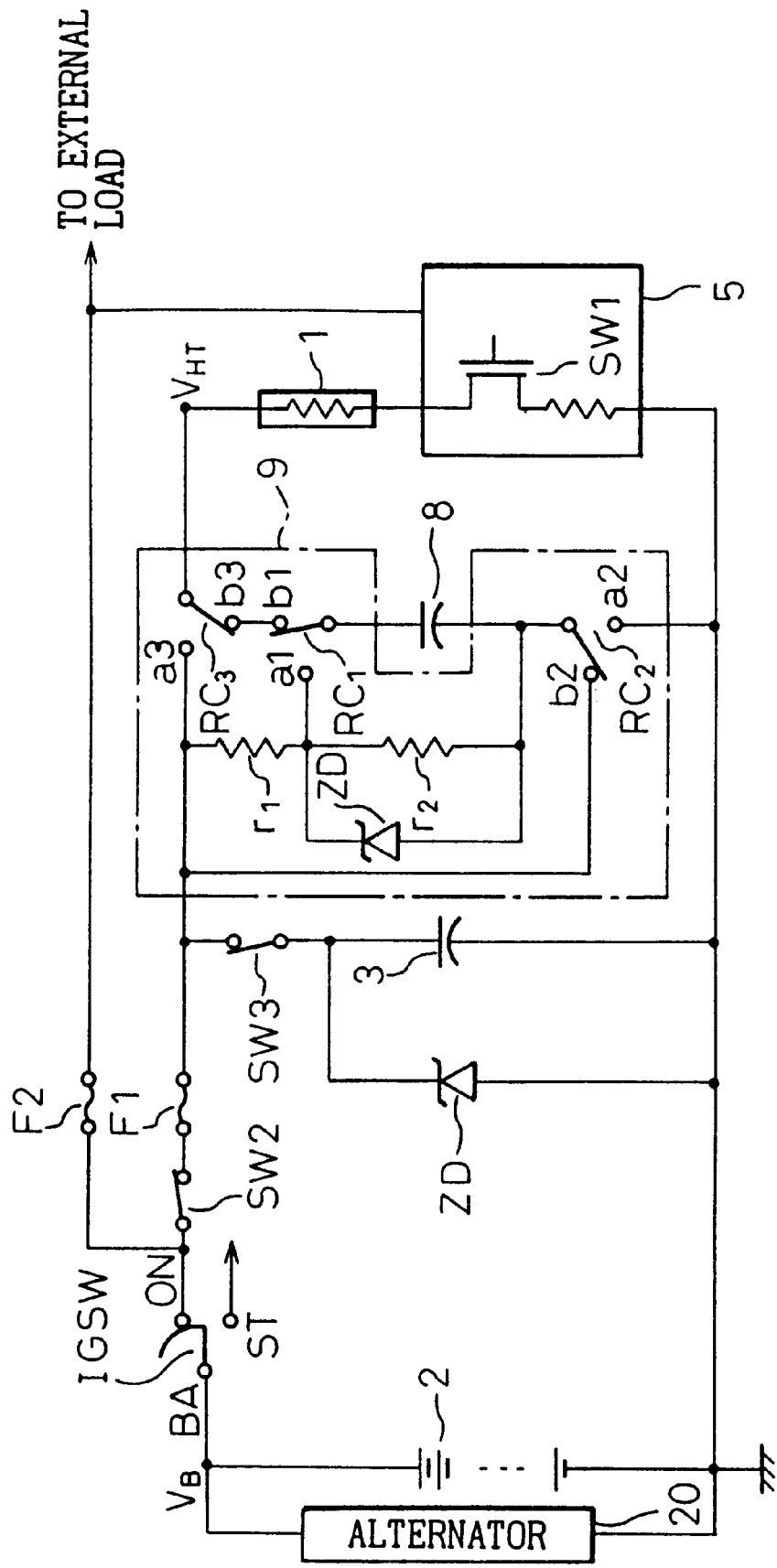
FIG. 14 is a diagram showing a configuration of a concrete example of the third aspect of the invention.
Figure 15A:
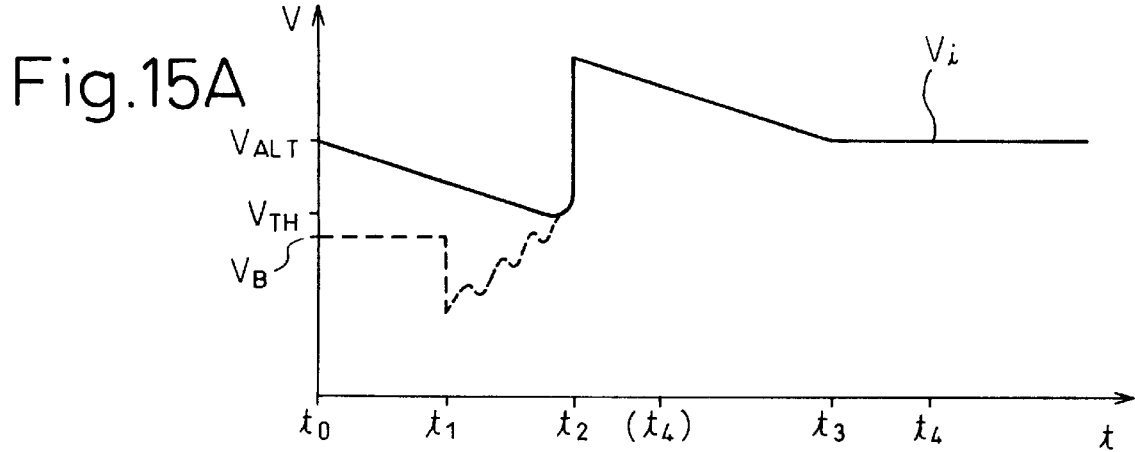
FIG. 15A is a time chart of the voltage applied to the heater according to the first control method in a concrete example of the third aspect of the invention.
Figure 15B:
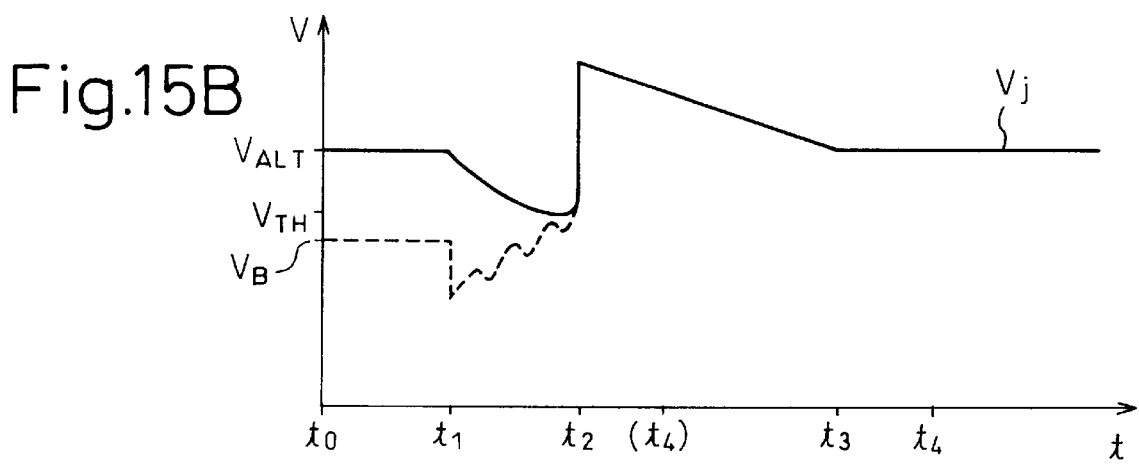
FIG. 15B is a time chart of the voltage applied to the heater according to the second control method in a concrete example of the third aspect of the invention.
Figure 15C:
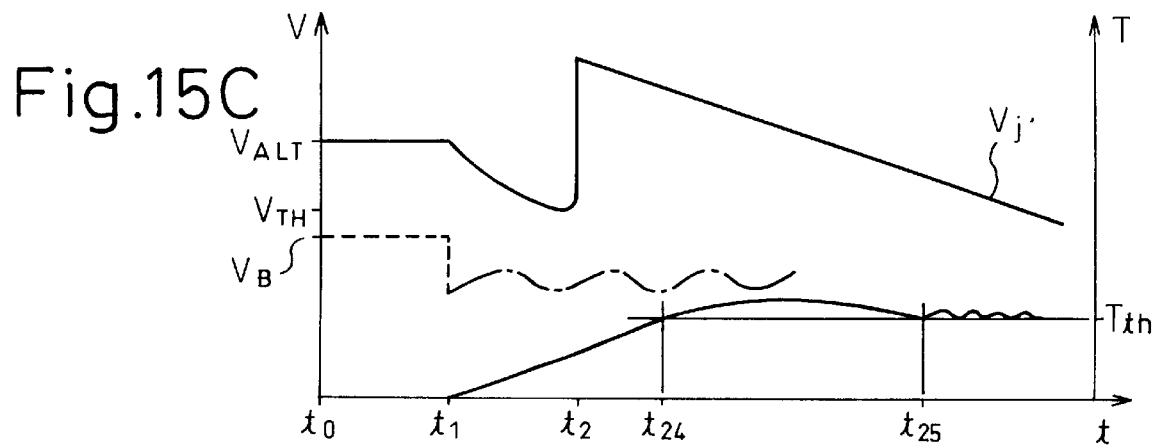
FIG. 15C is a time chart of the voltage applied to the heater according to the third control method in a concrete example of the third aspect of the invention.

FIG. 14 is a diagram showing a configuration of a concrete example of the third aspect of the invention, FIG. 15A is a time chart of the voltage applied to the heater according to a first control method, FIG. 15B is a time chart of the voltage applied to the heater according to a second control method, and FIG. 15C is a time chart of the voltage applied to the heater according to a third control method. In the first control method, the heater begins to be supplied with current by a first capacitor circuit at the time point when the ignition switch IGSW is turned on, and begins to be supplied with current by a second capacitor circuit at the time point when the voltage across the battery reaches a level not affecting the cranking after the ignition switch IGSW is turned to the starter position. In the second control method, on the other hand, the heater begins to be supplied with current by the first capacitor circuit at the time point when the ignition switch IGSW is turned to the starter position, and subsequently begins to be supplied with current by the second capacitor circuit at the time point when the voltage across the battery reaches a level not affecting the cranking. In the third control method similar to the second control method, the energization of the heater is inhibited when the heater temperature exceeds a predetermined level.

The control means 5 illustrated in simplistic fashion in FIG. 14 is shown in detail in FIG. 4. The third concrete example according to the third aspect of the invention shown in FIG. 14 is so configured that the capacitor circuit 8 and the charge-discharge switching means 9 in the first concrete example of the second aspect shown in FIG. 6 are added to the configuration of the concrete example of the first aspect shown in FIG. 4. The capacitor circuit 8 and the charge-discharge switching means 9 are connected in parallel to a series circuit including the heater 1 and the control means 5 as in the configuration of FIG. 6. Also, all the component parts shown in FIG. 14 are identical to, and have the same functions as, the corresponding ones designated by the same reference numerals or the same symbols, respectively, in FIGS. 4 and 6, and therefore will not be described again. Now, the control operation of the current control circuit 13 will be explained with reference to FIGS. 15A, 15B and 15C.

In FIGS. 15A, 15B and 15C, the abscissa represents the time and the ordinate the voltage applied to the heater; curve $V_i$ shows the change with time of the voltage applied to the heater according to the first control method in which a current begins to be supplied from the capacitor circuit 3 to the heater 1 as soon as the ignition switch IGSW is turned on; curve $V_j$ shows the change with time of the voltage applied to the heater according to the second control method in which a current is not supplied to the heater 1 when the ignition switch IGSW is turned on but begins to be supplied when the ignition switch IGSW is turned to the starter position; and curve $V_{j'}$ shows the change with time of the voltage applied to the heater according to the third control method similar to the second control method, in which the switch SW1 is operated in accordance with the activation of the air-fuel ratio sensor in the case where the battery is degenerated.

First, the curve $V_i$ will be explained with reference to FIG. 15A. At time point $t_0$ when the ignition switch IGSW is turned on, the voltage $V_{ALT}$ which is the maximum output voltage of the alternator 20 is applied to the heater 1 from the capacitor circuit 3 charged in advance by the same voltage $V_{ALT}$ while the engine is running after being started. At the same time, the heater 1 begins to be supplied with current. Since the second switch SW2 is open, the electricity charged in the first capacitor circuit 3 is discharged to the heater 1. The voltage $V_{HT}$ applied to the heater 1 gradually drops due to the power consumption by the heater 1. In the case where the engine starts, i.e., the ignition switch IGSW is switched to position ST at time point $t_1$ within several seconds of normal time point $t_0$, then the ECU begins to drive the starter motor not shown. The voltage $V_B$ across the battery 2 thus sharply declines due to the activation current of the starter motor. Once the starter motor is activated, however, the current consumed in the starter motor is reduced. Thus, the alternator 20 generates power and begins to charge the battery 2 by the rotation of the starter motor at the time of starting the engine and by rotation of the engine after the engine starts. Consequently, the voltage $V_B$ across the battery 2 gradually rises at and after time point $t_1$, and after passing a predetermined voltage $V_{TH}$ not affecting the engine cranking at time point $t_2$, soon reaches the maximum output voltage $V_{ALT}$ of the alternator 20.

At this time point $t_2$, the relays $R_1$, $R_2$ and $R_3$ are deenergized and the charge-discharge switching circuit 9 is switched from charge to discharge mode. Then, the heater 1 is impressed with a high voltage equal to the sum of the voltage $V_B$ across the battery 2 and the voltage $r_2 \times V_{ALT}/(r_1+r_2)$ charged in advance to the second capacitor circuit 8 while the engine is running after it is started. At and after time point $t_2$, the electricity charged in the second capacitor circuit 8 as well as that in the capacitor circuit 3 is discharged through the heater 1 due to the power consumption by the heater 1, so that the voltage applied to the heater 1 gradually declines and soon reaches the maximum output voltage of the alternator 20 at time point $t_3$. At and after time point $t_3$, the relays $R_1$, $R_2$ and $R_3$ are excited and the charge-discharge switching circuit 9 is switched from discharge to charge mode, while at the same time supplying power to the heater 1 from the battery 2, the alternator 20 and the capacitor 3. After that, but before time point $t_4$, the sensor element reaches an activation temperature $T_{th}$ of, say, 650° C. indicating the active state thereof, thereby permitting measurement of the air-fuel ratio (A/F).

At and after time point $t_4$, the temperature of the heater 1 is controlled in such a manner as to keep the sensor element active. This concrete example uses a method of controlling the power supplied to the heater based on a power map prepared in accordance with the engine operating conditions. Alternatively, a method can be used in which the resistance value of the heater is measured and controlled at a constant level, or a method in which the resistance value of the sensor element is measured and controlled at a constant value. The method employed in the present concrete example for controlling the power supplied to the heater is identical to that in the example of the first aspect of the invention, and therefore will not be described any further. Incidentally, the time point $t_4$ at which the sensor element becomes active after the ignition switch IGSW is turned from the off to the on state at time point $t_0$ may arrive earlier than the time point $t_3$ at which the voltage applied to the heater 1 declines to the maximum output voltage $V_{ALT}$ of the alternator 20. In this way, as compared with the conventional system in which power begins to be supplied to the heater 1 by the voltage across the battery 2 at and after time point $t_2$, the first control method indicated by curve $V_i$ in the concrete example according to the third aspect of the invention is such that the heater 1 begins to be supplied at time point $t_0$ with current by the electricity charged in the capacitor 3 in advance and is impressed from time point $t_2$ with the sum of the voltage $V_B$ across the battery 2 and the voltage $r_2 \times V_{ALT}/(r_1+r_2)$ charged to the second capacitor circuit 8 in advance, thus an early activation of the air-fuel ratio sensor is made possible.

Now, the curve $V_j$ will be explained with reference to FIG. 15B. At time point $t_0$ when the ignition switch IGSW is turned on, the heater 1 is impressed with a voltage $V_{ALT}$ charged in advance in the capacitor circuit 3 while the engine is running after being started. At this time point, the heater 1 is not yet supplied with current, and therefore the voltage $V_{HT}$ applied to the heater 1 holds a voltage value $V_{ALT}$ higher than the voltage $V_B$ across the battery 2 as of time point $t_0$. Upon starting the engine, i.e., as soon as the ignition switch IGSW is turned to the start position at time point $t_1$, the ECU begins to drive the starter motor (not shown), and therefore the voltage $V_B$ across the battery 2 sharply declines due to the activation current of the starter motor. Once the starter motor is activated, however, the current consumed by the starter motor is reduced. Thus, the alternator 20 generates power and begins to charge the battery 2 by the rotation of the starter motor at the time of starting the engine and by the rotation of the engine after the engine starts. As a result, the voltage $V_B$ across the battery 2 gradually increases at and after time point $t_1$.

The voltage $V_{HT}$ applied to the heater 1 at time $t_1$, on the other hand, is the voltage $V_{ALT}$ of the first capacitor circuit 3 which the maximum output voltage $V_{ALT}$ of the alternator 20 at which the first capacitor circuit 3 is charged while the engine is running. At and after time point $t_1$, this voltage $V_{ALT}$ gradually declines due to the power consumption by the heater 1. At and after time point $t_1$, however, the voltage $V_B$ across the battery 2 that has increased due to the charging from the alternator 20, after passing the predetermined voltage $V_{TH}$ not affecting the engine cranking, reaches the maximum output voltage $V_{ALT}$ of the alternator 20 at time point $t_2$. At this time point $t_2$, the relays $R_1$, $R_2$ and $R_3$ are deenergized and the charge-discharge switching circuit 9 is turned from charge to discharge mode. Then, at time point $t_2$, the heater 1 is impressed with the sum of the voltage $V_B$ across the battery 2 and the voltage $r_2 \times V_{ALT}/(r_1+r_2)$ charged to the second capacitor circuit 8 while the engine is running after the engine is started. At and after time point $t_2$, the electricity charged in the second capacitor circuit 8 as well as that in the first capacitor circuit 3 is discharged through the heater 1 due to the power consumption by the heater 1. Thus the voltage $V_{HT}$ applied to the heater 1 gradually drops and soon reaches the maximum output voltage $V_{ALT}$ of the alternator 20 at time point $t_3$. At and after time point $t_3$, the relays $R_1$, $R_2$ and $R_3$ are energized and the charge-discharge switching circuit 9 is switched from discharge to charge mode, while at the same time supplying power to the heater 1 from the battery 2, the alternator 20 and the first capacitor circuit 3. The control operation performed at and after time point $t_4$ is similar to that described with reference to FIG. 15A and will not be described.

As described above, unlike in the conventional system in which power begins to be supplied to the heater 1 with the voltage across the battery at and after time point $t_2$, the second control method in the concrete example according to the third aspect of the invention indicated by curve $V_j$ in FIG. 15B is such that the heater 1 begins to be impressed at time point $t_1$ with the voltage $V_{ALT}$ charged in the first capacitor circuit 3, and the sum of the voltage $V_B$ across the battery 2 and the voltage $r_2 \times V_{ALT}/(r_1+r_2)$ charged in the second capacitor circuit 8 in advance is applied to the heater 1 from time point $t_2$. An early activation of the air-fuel ratio sensor thus is made possible.

In addition to the first control method or the second control method described above, the switch SW1 can be closed only when the cranking is stable in order to prevent the deterioration of the engine startability. Judgement as to whether the cranking is stable or not is made by detecting the engine speed, the change in engine speed, the voltage drop across the battery, the engine water temperature, etc., and by checking whether these values meet a predetermined reference value.

Now, the curve $V_{j'}$ will be explained with reference to FIG. 15C. The third control method shown in FIG. 15C is associated with the condition under which the battery is degenerated to such an extent as to cause a protracted engine cranking. The curve $V_{j'}$ in FIG. 15C, like the curve $V_j$ in FIG. 15B, shows the change with time of the voltage applied to the heater 1 in the case where the heater 1 is supplied with current not from the time when the ignition switch IGSW is turned on but from the time when the ignition switch IGSW is turned to the starter position. According to the third control method, the switch SW1 is opened in the case where the voltage $V_B$ across the battery 2 fails to reach a predetermined value before the same time point $t_2$ shown in FIG. 15B after starting cranking at time point $t_1$ and the air-fuel ratio sensor element reaches an activation temperature $T_{th}$ of, say, 650° C. indicating the active state thereof at time point $t_{24}$ during the cranking, thus making possible measurement of the air-fuel ratio (A/F). After that, in order to maintain the active state of the air-fuel ratio sensor element, the heater temperature control is suspended. In other words, the switch SW1 is operated in accordance with a power map prepared in accordance with the engine operating conditions to stop supplying power to the heater 1. The switch SW1 is closed again and the heater temperature control is resumed at and after time point $t_{25}$ when the heater temperature calculated from the resistance value of the heater 1 declines to or below the predetermined temperature of 650° C. This process is repeated. The third control method thus can prevent the battery 2 from being excessively consumed which otherwise might be the case due to the heating of the heater 1.

In the third aspect of the invention, it is also possible to detect the voltage applied to the heater 1 when the switch SW2 is open and the charge-discharge switching circuit 9 is turned to set the second capacitor circuit 8 in charged state, to determine a fault in the first capacitor circuit 3 from the voltage thus detected, and thereby to indicate a first fault of the first capacitor circuit 3 by lighting a display lamp, for example.

Also, in the third aspect of the invention, it is possible to detect the voltage applied to the heater 1 each time the charge-discharge switching circuit 9 is turned to set the second capacitor circuit 8 in charged state or in discharged state, to use the difference of the detected voltages for detecting a fault in the second capacitor circuit in the case where the voltage in the beginning of discharge fails to become higher than the voltage at the time of charging by an amount equivalent to the voltage charged in the second capacitor circuit 8, for example, and thereby to indicate a second fault in the second capacitor circuit 8 by lighting a display lamp, for example.

Further, the system can comprise a third switch SW3 adapted to be connected in series with the first capacitor circuit 3 after the first fault diagnosis of the third capacitor circuit 3 for supplying or cutting off the charge current and the discharge current for the first capacitor circuit 3. Upon fault detection, the switch SW1 is controlled to close at the end of engine cranking while the switch SW3 is kept normally open, thereby securing the reliability of the system.

Furthermore, after the second fault diagnosis of the second capacitor circuit 8, the switch SW1 can be controlled to close at the end of engine cranking, and at least one of the terminals of the second capacitor circuit 8 connected to the charge-discharge circuit 9 is switched to normally open state, thereby securing the reliability of the system. For controlling at least one of the terminals of the second capacitor circuit 8 to turn to normally open state, a contact point $RC_n$ of a new relay $R_n$ not shown is inserted between the positive terminal of the second capacitor circuit 8 and the common terminal c of the contact $RC_1$ of the relay $R_1$, and this contact point $RC_n$ which is normally closed is opened when a fault of the second capacitor circuit 8 is detected.

A concrete example of the third aspect of the invention was described above with reference to FIG. 14. It will, however, be easily understood to those skilled in the art that other concrete examples of the third aspect of the invention can be easily configured, as in the concrete example of the second aspect, by replacing the capacitor circuit 8 and the charge-discharge switching circuit 9 shown in FIGS. 8, 9 and 10 with the capacitor circuit 8 and the charge-discharge switching circuit 9, respectively, shown in FIG. 14. Such other concrete examples, therefore, will not be described in detail.

As will be understood from the foregoing description, according to the third aspect of the invention, there is provided a heater control system for an air-fuel ratio sensor of an internal combustion engine, in which a first capacitor circuit is isolated from a battery and an alternator when the engine is started but connected in parallel to the battery and the alternator and charged at a maximum output voltage of the alternator higher than the battery voltage while the engine is running, and in which power is supplied to a heater when the engine is started at a high voltage produced by superimposing a charge voltage of the first capacitor circuit on a charge voltage of a second capacitor circuit charged in advance while the engine is running. As a result, an early activation of the air-fuel ratio sensor at the time of starting the engine can be realized while at the same time suppressing the deterioration of the exhaust emission at an early time.

Figure 16:
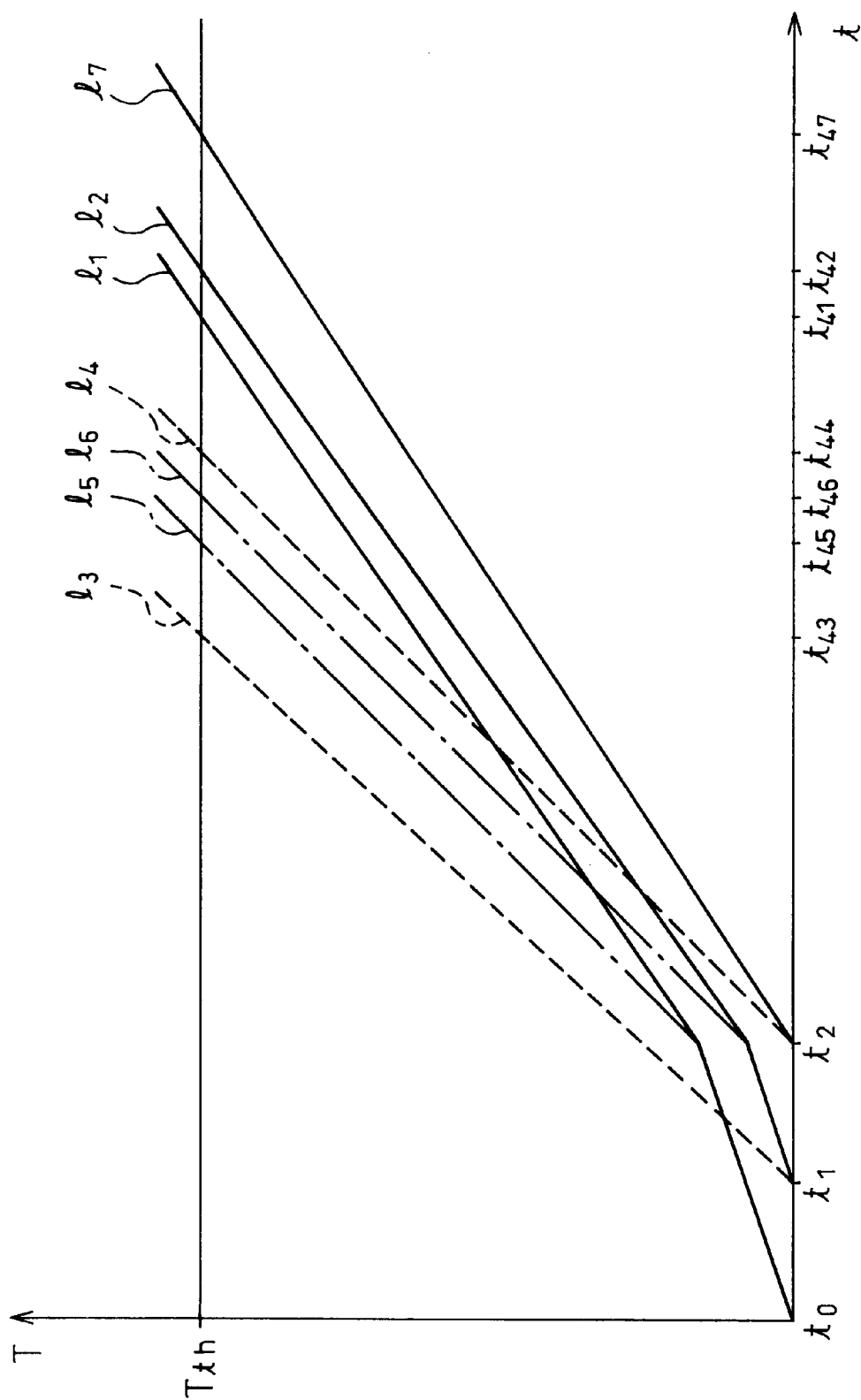
FIG. 16 is a time chart showing the temperature change of the air-fuel ratio sensor element from the time when the engine starts to the time when the air-fuel ratio sensor is activated according to the first to third aspects of the invention as compared with that for the conventional systems.
Figure 17:
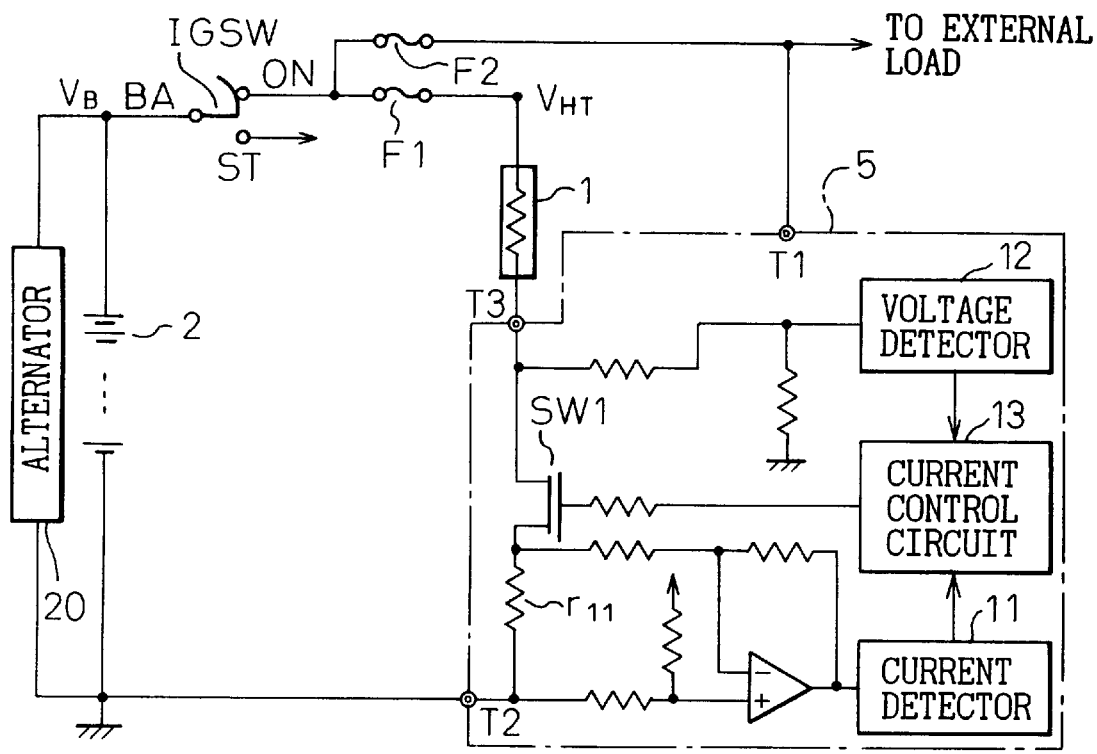
FIG. 17 is a schematic diagram showing a configuration of a conventional heater control system for an air-fuel ratio sensor of an internal combustion engine.
Figure 18:
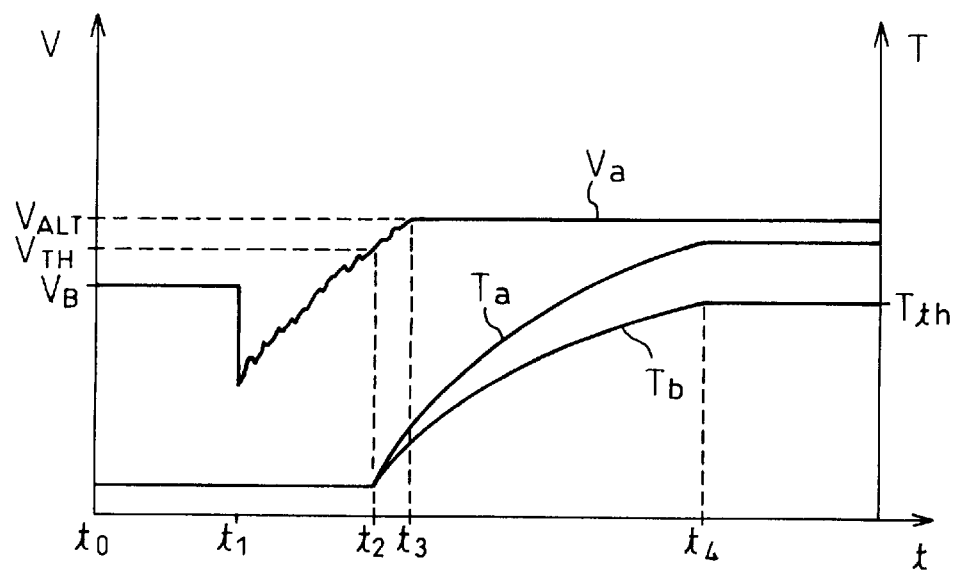
FIG. 18 is a time chart of the voltage applied to the heater, the heater temperature and the temperature of the sensor element in the heater control system shown in FIG. 17.

FIG. 16 is a time chart showing the temperature change of the air-fuel ratio sensor element until activation of the air-fuel ratio sensor from the time of starting the engine according to the first to third aspects of the invention as compared with the prior art. In this time chart, the abscissa represents the heating time of the heater, and the ordinate represents the temperature of the air-fuel ratio sensor element. The temperature change of the air-fuel ratio sensor element according to the first control method of the first aspect, the second control method of the first aspect and the prior art are indicated by solid lines $l_1$, $l_2$, $l_7$, respectively. The first control method of the second aspect and the second control method of the second aspect of the invention are indicated by dashed line $l_3$, $l_4$, respectively. The first control method of the third aspect and the second control method of the third aspect are indicated by one-dot chains $l_5$, $l_6$, respectively. $t_0$ designates the time point when the ignition switch IGSW is turned from the off to the on state, $t_1$ the time point when the ignition switch IGSW is switched from the on state to the starter mode, $t_2$ the time point when the battery voltage has increased to the voltage $V_{TH}$ not affecting the cranking, and $t_{41}$, $t_{42}$, $t_{43}$, $t_{44}$, $t_{45}$, $t_{46}$ and $t_{47}$ the time points when the air-fuel ratio sensor element has reached the activation temperature $T_{th}$ by controlling the heating process of the heater according to the first and the second control methods of the first aspect, the first and the second control methods of the second and aspect, the first and the second control methods of the third aspect, and the prior art, respectively. It is seen from this diagram that the first to third aspects of the invention can activate the air-fuel ratio sensor element earlier than the prior art at the time of starting the engine.

It will be understood by those skilled in the art that the foregoing descriptions are preferred embodiments of the disclosed system and that various changes and modifications may be made in the invention without departing from the spirit and scope thereof.

What is claimed is:

1. An air-fuel ratio sensor system of an internal combustion engine including heater control means, comprising:
   an air-fuel ratio sensor arranged in the exhaust system of an internal combustion engine for detecting the air-fuel ratio of the internal combustion engine;
   a heater for heating said air-fuel ratio sensor;
   a power supply for supplying power to said heater;
   a first switch for opening or closing a power line for transmitting power to a load including said heater from said power supply;
   power control means for controlling the power supplied to said heater in such a manner as to maintain said air-fuel ratio sensor in active state;
   a capacitor circuit charged by said power supply and adapted to discharge through said heater the electricity stored by said charging, said capacitor circuit capable of being selectively connectable to said heater so as to be a sole power supply to said heater;
   a second switch interposed between said power supply and said capacitor circuit for supplying or cutting off a charge current to said capacitor circuit from said power supply;
   a third switch connected in series to said heater for supplying or cutting off the current flowing to said heater from at least one of said power supply and said capacitor circuit; and
   switching control means for controlling said third switch to close after said first switch is closed.

2. A system according to claim 1, wherein said switching control means controls said third switch to close from the time when the engine starts cranking.

3. A system according to claim 2, further comprising fault judging means for detecting the voltage applied to said heater when said second switch is open and judging a fault of said capacitor circuit from said detected voltage.

4. A system according to claim 1, wherein said switching control means controls said third switch to operate in accordance with the engine cranking condition after said power switch is closed.

5. A system according to claim 4, further comprising fault judging means for detecting the voltage applied to said heater when said second switch is open and judging a fault of said capacitor circuit from said detected voltage.

6. A system according to claim 1, wherein said switching control means controls said third switch to open when the temperature of said heater exceeds a predetermined level and to close when the temperature of said heater is not higher than the predetermined level during the engine cranking after said third switch is closed.

7. A system according to claim 6, further comprising fault judging means for detecting the voltage applied to said heater when said second switch is open and judging a fault of said capacitor circuit from said detected voltage.

8. A system according to claim 1, further comprising fault judging means for detecting the voltage applied to said heater when said second switch is open and judging a fault of said capacitor circuit from said detected voltage.

9. A system according to claim 8, further comprising a fourth switch connected in series to said capacitor circuit, for supplying or cutting off the charge current and the discharge current of said capacitor circuit, wherein upon a fault judgment by said fault judging means, said switching control means controls said third switch to be closed after the end of engine cranking and controls said fourth switch to be set in normally open state.

10. An air-fuel ratio sensor system of an internal combustion engine including heater control means, comprising:
    an air-fuel ratio sensor arranged in the exhaust system of an internal combustion engine for detecting the air-fuel ratio of the internal combustion engine;
    a heater for heating said air-fuel ratio sensor,
    a power supply for supplying power to said heater;
    a first switch for opening or closing a power line for transmitting power to a load including said heater from said power supply;
    power control means for controlling the power supplied to said heater in such a manner as to maintain said air-fuel ratio sensor in active state;
    a capacitor circuit charged by said power supply and adapted to discharge through said heater the electricity stored by said charging, said capacitor circuit capable of being selectively connectable to said heater so as to be a sole power supply to said heater;
    a second switch interposed between said power supply and said capacitor circuit for supplying or cutting off a charge current to said capacitor circuit from said power supply;
    a charge-discharge switching circuit for connecting said power supply in parallel to said capacitor circuit and connecting said heater in series to said parallel circuit including said power supply and said capacitor circuit thereby to form a charge circuit at the time of charging said capacitor circuit, and for connecting said power supply, said capacitor circuit and said heater in series to each other thereby to form a discharge circuit at the time of discharging said capacitor circuit;
    a third switch connected in series to said heater for supplying or cutting off the current flowing into said heater; and
    switching control means for controlling said third switch to close at the time of starting the engine cranking after said first switch is closed, said switching control means switching said charge-discharge switching circuit to form said charge circuit when said air-fuel ratio sensor is active and switching said charge-discharge switching circuit to form said discharge circuit when said air-fuel ratio sensor is inactive.

11. A system according to claim 10, wherein said switching control means controls said third switch to close and switches said charge-discharge switching circuit from said charge circuit to said discharge circuit after the end of engine cranking.

12. A system according to claim 11, further comprising a fault judging circuit for detecting the voltage applied to said heater at the time of charging and discharging said capacitor circuit and judging a fault of said capacitor circuit from the difference of the voltages thus detected.

13. A system according to claim 12, wherein upon a fault judgement by said fault judging means, said switching control means controls said third switch to close after the end of engine cranking and to switch to a normally open state at least one of the terminals of said capacitor circuit connected to said charge-discharge switching circuit.

14. A system according to claim 10, further comprising a fault judging circuit for detecting the voltage applied to said heater at the time of charging and discharging said capacitor circuit and judging a fault of said capacitor circuit from the difference of the voltages thus detected.

15. A system according to claim 14, wherein upon a fault judgement by said fault judging means, said switching control means controls said third switch to close after the end of engine cranking and to switch to a normally open state at least one of the terminals of said capacitor circuit connected to said charge-discharge switching circuit.

16. A system according to claim 10, wherein said capacitor circuit includes a plurality of capacitors connected in parallel to each other.

17. A system according to claim 10, wherein said capacitor circuit includes a plurality of capacitors connected in series with each other.

18. A system according to claim 17, further comprising a resistor adapted to be interposed between the negative electrode of said capacitor and the ground at the time of charging said capacitor circuit.

19. A system according to claim 10, further comprising a diode adapted to be connected to said power line in parallel to said capacitor circuit at the time of discharging said capacitor circuit.

20. A system according to claim 10, wherein said capacitor circuit includes a plurality of capacitors, said system further comprising switching means for switching the discharge voltage pattern of said capacitor circuit.

21. A system according to claim 20, wherein said switching means includes at least a switch, and said capacitor circuit is switched between series connection and parallel connection by operating said switch.

22. A system according to claim 20, wherein said switching means includes a switch and the discharge of a part of said capacitors is inhibited by operating said switch.

23. A system according to claim 20, wherein all the capacitors of said capacitor circuit are connected in series at the time of charging, said system further comprising a resistor inserted between the negative electrode of said capacitor circuit and the ground.

24. An air-fuel ratio sensor system of an internal combustion engine including heating control means, comprising:
   an air-fuel ratio sensor arranged in the exhaust system of an internal combustion engine for detecting the air-fuel ratio of the internal combustion engine;
   a heater for heating said air-fuel ratio sensor;
   a power supply for supplying power to said heater;
   a first switch for opening or closing a power line for transmitting power to a load including said heater from said power supply;
   power control means for controlling the power supplied to said heater in such a manner as to maintain said air-fuel ratio sensor in active state;
   a capacitor circuit charged by said power supply and adapted to discharge through said heater the electricity stored by said charging, said capacitor circuit capable of being selectively connectable to said heater so as to be a sole power supply to said heater; and
   a second switch interposed between said power supply and said capacitor circuit for supplying or cutting off a charge current to said capacitor circuit from said power supply;
   wherein said capacitor circuit includes a first capacitor circuit and a second capacitor circuit charged by said power supply and adapted to discharge through said heater the electricity stored therein by said charging, said system further comprising:
   a charge-discharge switching circuit for connecting said second capacitor circuit in parallel to said first capacitor circuit connected in parallel to said power supply and connecting said heater in series to said parallel circuit including said power supply and said first and second capacitors thereby to form a charge circuit at the time of charging said second capacitor circuit, and for connecting said second capacitor circuit and said heater in series to said first capacitor circuit connected in parallel to said power supply thereby to form a discharge circuit at the time of discharging said second capacitor circuit;
   a third switch connected in series to said heater for supplying or cutting off the current flowing to said heater; and
   switching control means for controlling said third switch to close after said first switch is closed, and for controlling said charge-discharge switching circuit from the beginning of engine cranking in such a manner as to form said charge circuit when said air-fuel ratio sensor is active and to form said discharge circuit when said air-fuel ratio sensor is inactive.

25. A system according to claim 24, wherein said switching control means controls said third switch to close from the beginning of engine cranking.

26. A system according to claim 25, further comprising a first fault judging means for detecting the voltage applied to said heater when said second switch is open and for judging a fault of said first capacitor circuit from said detected voltage.

27. A system according to claim 24, wherein said switching control means controls said third switch to operate in accordance with the engine cranking condition after said first switch is closed.

28. A system according to claim 27, further comprising a first fault judging means for detecting the voltage applied to said heater when said second switch is open and for judging a fault of said first capacitor circuit from said detected voltage.

29. A system according to claim 24, further comprising heater temperature detection means, wherein said switching control means controls said third switch to open when the heater temperature exceeds a predetermined level and to close when the heater temperature is not higher than said predetermined level during the engine cranking after said third switch is closed.

30. A system according to claim 29, further comprising a first fault judging means for detecting the voltage applied to said heater when said second switch is open and for judging a fault of said first capacitor circuit from said detected voltage.

31. A system according to claim 24, further comprising a first fault judging means for detecting the voltage applied to said heater when said second switch is open and for judging a fault of said first capacitor circuit from said detected voltage.

32. A system according to claim 31, further comprising a fourth switch connected in series to said first capacitor circuit for supplying or cutting off the charge current and the discharge current of said first capacitor circuit,
   wherein upon a fault judgement by said first fault judging means, said control means controls said first switch to close from the end of engine cranking and to turn said third switch to a normally open state.

33. A system according to claim 24, further comprising a second fault judging means for detecting the voltage applied to said heater at the time of charging and discharging said first capacitor circuit and said second capacitor circuit and for judging a fault of said second capacitor circuit from the detected difference of said voltages.

34. A system according to claim 33, wherein upon a fault judgement by said second fault judging means, said switching control means controls said third switch to close after the end of engine cranking and to switch to a normally open state at least one of the terminals of said second capacitor circuit connected to said charge-discharge switching circuit.

35. A system according to claim 24, wherein said second capacitor circuit includes a plurality of capacitors connected in parallel to each other.

36. A system according to claim 24, wherein said second capacitor includes a plurality of capacitors connected in series with each other.

37. A system according to claim 36, further comprising a resistor adapted to be interposed between the negative electrode of said second capacitor circuit and the ground at the time of charging said second capacitor circuit.

38. A system according to claim 24, further comprising a diode adapted to be connected to a power line in parallel to said second capacitor circuit at the time of discharging said second capacitor circuit.

39. A system according to claim 24, wherein said second capacitor circuit includes a plurality of capacitors, said system further comprising switching means for switching the discharge voltage pattern of said second capacitor circuit.

40. A system according to claim 39, wherein said switching means includes at least a switch and said second capacitor circuit is switched between series connection and parallel connection by operating said switch.

41. A system according to claim 39, wherein said switching means includes a switch and the discharge of a part of said capacitors is inhibited by operating said switch.

42. A system according to claim 39, wherein all the capacitors of said second capacitor circuit are connected in series with each other at the time of charging, said system further comprising a resistor interposed between the negative electrode of said second capacitor circuit and the ground.

* * * * *